United States Patent
Duan et al.

(10) Patent No.: US 9,637,455 B2
(45) Date of Patent: May 2, 2017

(54) HETEROCYCLIC SULFONE RORγ MODULATORS

(71) Applicant: BRISTOL-MYERS SQUIBB COMPANY, Princeton, NJ (US)

(72) Inventors: Jingwu Duan, Yardley, PA (US); T. G. Murali Dhar, Newtown, PA (US); Bin Jiang, Bryn Mawr, PA (US); Ananta Karmakar, Bangalore (IN); Arun Kumar Gupta, Bangalore (IN); Zhonghui Lu, King of Prussia, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/109,727

(22) PCT Filed: Jan. 5, 2015

(86) PCT No.: PCT/US2015/010090
§ 371 (c)(1),
(2) Date: Jul. 5, 2016

(87) PCT Pub. No.: WO2015/103510
PCT Pub. Date: Jul. 9, 2015

(65) Prior Publication Data
US 2016/0326115 A1    Nov. 10, 2016

Related U.S. Application Data

(60) Provisional application No. 61/923,904, filed on Jan. 6, 2014.

(51) Int. Cl.

| | | |
|---|---|---|
| *C07D 211/54* | (2006.01) | |
| *C07D 309/08* | (2006.01) | |
| *C07D 401/06* | (2006.01) | |
| *C07D 405/06* | (2006.01) | |
| *C07D 211/96* | (2006.01) | |
| *A61K 31/352* | (2006.01) | |
| *A61K 31/4418* | (2006.01) | |

(52) U.S. Cl.
CPC .......... *C07D 211/54* (2013.01); *C07D 211/96* (2013.01); *C07D 309/08* (2013.01); *C07D 401/06* (2013.01); *C07D 405/06* (2013.01)

(58) Field of Classification Search
None
See application file for complete search history.

(56) References Cited

U.S. PATENT DOCUMENTS

| | | |
|---|---|---|
| 2,802,013 A | 8/1957 | Dodson et al. |
| 2,812,330 A | 11/1957 | Dodson et al. |
| 3,016,403 A | 1/1962 | Dodson et al. |
| 9,458,171 B2 | 10/2016 | Duan et al. |

FOREIGN PATENT DOCUMENTS

| | | | | |
|---|---|---|---|---|
| DE | 735 866 | 6/1943 | | |
| EP | 1 466 898 | 10/2004 | | |
| GB | WO 02081435 A1 * | 10/2002 | ........... | C07C 317/14 |
| WO | WO 02/081435 | 10/2002 | | |
| WO | WO 2013/092939 | 6/2013 | | |
| WO | WO 2013/169588 | 11/2013 | | |
| WO | WO 2014/028669 | 2/2014 | | |
| WO | WO 2014028669 A1 * | 2/2014 | ........... | C07D 213/75 |
| WO | WO2014/062938 | 4/2014 | | |
| WO | WO2015/035278 | 3/2015 | | |
| WO | WO2015/042212 | 3/2015 | | |
| WO | WO2015/103507 | 7/2015 | | |
| WO | WO2015/103508 | 7/2015 | | |
| WO | WO2015/103509 | 7/2015 | | |
| WO | WO2015/103510 | 7/2015 | | |

OTHER PUBLICATIONS

Hörig et al., J. Translational Med. 2:44 (2004).*
Close et al., Bioorganic & Medicinal Chemistry letters, vol. 22, No. 9, pp. 3203-3207 (2012).
Evans et al., European Journal of Organic Chemistry, vol. 2006, No. 7, pp. 1740-1754 (2006).
Thijs et al., Tetrahedron Letters, vol. 14, No. 37, pp. 3589-3592 (1973).
Der Pharma Chemica et al., pp. 438-445 (Jan. 1, 2010) Retrieved from the internet: http:derpharmachemica.com/vol2-iss5/DPC-2010-2-5-438-445.pdf.
Capuano et al., Chemische Berichte, vol. 112, No. 3 pp. 1012-1022 (1979).
Golinski et al., Synthesis, No. 11, pp. 823-825 (1978).

(Continued)

*Primary Examiner* — Michael Barker
(74) *Attorney, Agent, or Firm* — Elliott Korsen

(57) ABSTRACT

Described are RORγ modulators of the formula (I), [INSERT CHEMICAL STRUCTURE HERE] or stereoisomers, tautomers, pharmaceutically acceptable salts, solvates, or prodrugs thereof, wherein all substituents are defined herein. Also provided are pharmaceutical compositions comprising the same. Such compounds and compositions are useful in methods for modulating RORγ activity in a cell and methods for treating a subject suffering from a disease or disorder in which the subject would therapeutically benefit from modulation of RORγ activity, for example, autoimmune and/or inflammatory disorders.

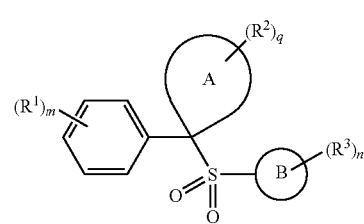

3 Claims, No Drawings

(56) References Cited

OTHER PUBLICATIONS

Meek et al., Journal of Organic Chemistry, vol. 33, No. 9, pp. 3418-3421 (1968).

* cited by examiner

HETEROCYCLIC SULFONE RORγ MODULATORS

CROSS-REFERENCE TO RELATED APPLICATIONS

This application claims the benefit of U.S. Provisional Application No. 61/923,904, filed Jan. 6, 2014, the disclosure of which is incorporated herein by reference in its entirety.

FIELD OF THE INVENTION

This invention relates to modulators of the retinoid-related orphan receptor RORγ and methods for using such modulators. The compounds described herein can be particularly useful for diagnosing, preventing, or treating a variety of diseases and disorders in humans and animals. Exemplary disorders include, but are not limited to, psoriasis, rheumatoid arthritis, inflammatory bowel disease, Crohn's disease, ulcerative colitis, acute graft-versus-host disease, psoriatic arthritis, ankylosing spondylitis and multiple sclerosis.

BACKGROUND OF THE INVENTION

The retinoid-related orphan receptors RORα, RORβ, and RORγ play an important role in numerous biological processes including organ development, immunity, metabolism, and circadian rhythms. See, for example, Dussault et al. in Mech. Dev. (1998) vol. 70, 147-153; Andre et al. in EMBO J. (1998) vol. 17, 3867-3877; Sun et al. in Science (2000) vol. 288, 2369-2373; and Jetten in Nucl. Recept. Signal. (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in Biochem. Biophys. Res. Commun. (1994) vol. 205, 1976-1983; Oritz et al. in Mol. Endocrinol. (1995) vol. 9, 1679-1691; and He et al. in Immunity (1998) vol. 9, 797-806. Expression of RORγt is restricted to lymphoid cell types including CD4+CD8+ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γδ, and LTi cells. See, for example, Sun et al. in Science (2000) vol. 288, 2369-2373; Ivanov et al. in Cell (2006) vol. 126, 1121-1133; Eberl et al. in Nat. Immunol. (2004) vol. 5, 64-73; Ivanov et al. in Semin. Immunol. (2007) vol. 19, 409-417; and Cua and Tato in Nat. Rev. Immunol. (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracellular pathogens. See, for example, Ivanov et al. in Semin. Immunol. (2007) vol. 19: 409-417; and Marks and Craft in Semin. Immunol. (2009) vol. 21, 164-171. RORγ directly regulates IL-17 transcription and disruption of RORγ in mice attenuates IL-17 production. See, for example, Ivanov et al. in Cell (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in Nat. Med. (2002) vol. 8, 500-508; Tzartos et al. in Am. J. Pathol. (2008) vol. 172, 146-155; Kotake et al. in J. Clin. Invest. (1999) vol. 103, 1345-1352; Kirkham et al. in Arthritis Rheum. (2006) vol. 54, 1122-1131; Lowes et al. in J. Invest. Dermatol. (2008) vol. 128, 1207-1211; Leonardi et al. in N. Engl. J. Med. (2012) vol. 366, 1190-1199; Fujino et al. in Gut (2003) vol. 52, 65-70; Seiderer et al. in Inflamm. Bowel Dis. (2008) vol. 14, 437-445; Wong et al. in Clin. Exp. Immunol. (2001) vol. 125, 177-183; and Agache et al. in Respir. Med. (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in Ann. N.Y. Acad. Sci. (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in Cell (2006) vol. 126, 1121-1133; Yang et al. in Immunity (2008) vol. 28, 29-39; Pantelyushin et al. in J. Clin. Invest. (2012) vol. 122, 2252-2256; Leppkes et al. in Gastroenterology (2009) vol. 136, 257-267; and Tilley et al. in J. Immunol. (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of the formula (I),

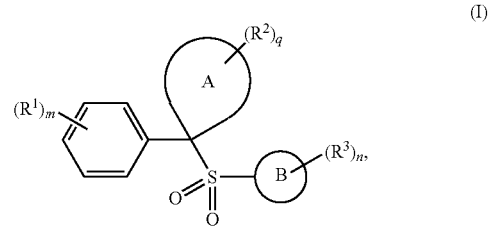

or pharmaceutically acceptable salts thereof, wherein all substituents are defined herein. The invention includes stereoisomers, tautomers, pharmaceutically acceptable salts, solvates, or prodrugs thereof.

In another aspect, the invention comprises pharmaceutical compositions comprising a compound according to formula (I), stereoisomeric form or pharmaceutically acceptable salt, as described herein, and a pharmaceutically acceptable carrier, excipient, or diluent.

In another aspect, the invention comprises methods for antagonizing RORγ in a cell comprising contacting the cell with an effective amount of a compound according to formula (I), stereoisomeric form or pharmaceutically acceptable salt, as described herein. This aspect may be conducted in vitro or in vivo.

In another aspect, the invention comprises methods for treating a subject suffering from a disease or disorder modulated by RORγ, the method comprising administering to a subject a therapeutically effective amount of compound according to formula (I), stereoisomeric form, pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of compound according to formula (I), or a stereoisomeric form, pharmaceutically acceptable salt or pharmaceutical composition as described herein.

DETAILED DESCRIPTION OF THE INVENTION

In one aspect, the invention comprises compounds of formula (I),

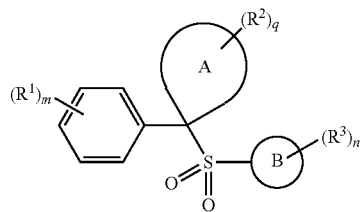

I or a stereoisomer or pharmaceutically-acceptable salt thereof,
wherein
A is a 3-7 membered heterocycle comprising carbon atoms, and 1-4 heteroatoms selected from N, O, and $S(O)_p$, provided that if B is phenyl, A is not

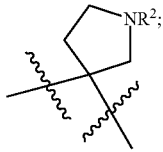

B is a, —$(CH_2)_r$-3-14 membered carbocycle, or —$(CH_2)_r$-5-12 membered heterocycle comprising carbon atoms, and 1-4 heteroatoms selected from N, O, and $S(O)_p$;

$R^1$ is selected from H, halo, $C_{1-6}$ alkyl substituted with 0-3 $R^{1a}$ and —$(CH_2)_r$-3-14 membered carbocycle substituted with 0-3 $R^{1a}$;

$R^{1a}$ is, independently at each occurrence, hydrogen, =O, halo, $CF_3$, $OCF_3$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle substituted with 0-3 $R^a$, or —$(CH_2)_r$-5-7 membered heterocycle comprising carbon atoms, and 1-4 heteroatoms selected from N, O, and $S(O)_p$ substituted with 0-3 $R^a$;

$R^2$ is selected from hydrogen, —$(CH_2)_rC(O)R^{2d}$, —$(CH_2)_rC(O)OR^{2b}$, —$(CH_2)_rC(O)NR^{11}R^{11}$, —$(CH_2)_rS(O)_2R^2$, —$(CH_2)_rS(O)_pNR^{11}R^{11}$, $C_{1-6}$ alkyl substituted with 0-3 $R^{2a}$, $C_{2-6}$ alkenyl substituted with 0-3 $R^{2a}$, —$(CH_2)_r$-3-10 membered carbocycle substituted with 0-3 $R^a$, and —$(CH_2)_r$-4-7 membered heterocycle comprising carbon atoms, and 1-4 heteroatoms selected from N, O, and $S(O)_p$ substituted with 0-3 $R^a$;

$R^{2a}$ is, independently at each occurrence, hydrogen, =O, halo, $OCF_3$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $(CH_2)_r$-3-14 membered carbocycle substituted with 0-3 $R^a$, or —$(CH_2)_r$-4-7 membered heterocycle comprising carbon atoms and 1-4 heteroatoms selected from N, O, and $S(O)_p$ substituted with 0-3 $R^a$;

$R^{2b}$ is, independently at each occurrence, hydrogen, $CF_3$, —$(CH_2)_rOR^b$, —$(CH_2)_rS(O)_pR^b$, —$(CH_2)_rC(O)R^{1d}$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^{1c}$, —$(CH_2)_rNR^bC(O)OR^c$, —$(CH_2)_rNR^bC(O)NR^{11}R^{11}$, —$(CH_2)_rS(O)_2NR^{11}R^{11}$, —$(CH_2)_rNR^bS(O)_2R^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-2 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CH_2)_r$ 5-10 membered heterocycle containing 1-4 heteroatoms selected from N, O, and $S(O)_p$, substituted with 0-3 $R^a$;

$R^{2d}$ is, independently at each occurrence, hydrogen, $C_{1-6}$ alkyl substituted with 0-2 $R^d$, $C_{1-6}$ haloalkyl, —C(O)$NR^{11}R^{11}$, $C_{3-6}$ cycloalkyl substituted with 0-2 $R^d$, —$(CH_2)_r$-phenyl substituted with 0-2 $R^a$, or a 5-10 membered heterocycle containing 1-4 heteroatoms selected from N, O, and $S(O)_p$, substituted with 0-3 $R^a$;

$R^3$ is selected from hydrogen, halo, $N_3$, CN, —$(CH_2)_rOR^{3b}$, —$(CH_2)_rNR^{11}R^{11}$, $C_{1-6}$ alkyl substituted with 0-3 $R^{3a}$, and $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CH_2)_r$-3-14 membered carbocycle substituted with 0-3 $R^a$, or a —$(CH_2)_r$-5-10 membered heterocycle comprising carbon atoms and 1-4 heteroatoms selected from N, O, and $S(O)_p$ substituted with 0-3 $R^a$;

$R^{3b}$ is, independently at each occurrence, $CF_3$, —$(CH_2)_rOR^b$, —$(CH_2)_rSR^b$, —$(CH_2)_rC(O)R^{1d}$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^{1c}$, —$(CH_2)_rNR^bC(O)OR^c$, —$(CH_2)_rNR^bC(O)NR^{11}R^{11}$, —$(CH_2)_rS(O)_2NR^{11}R^{11}$, —$(CH_2)_rNR^bS(O)_2R^c$, —$(CH_2)_rS(O)R^c$, —$(CH_2)_rS(O)_2R^c$, $C_{1-6}$ alkyl substituted with 0-3 $R^a$, $C_{1-6}$ haloalkyl, —(CH$_2$)$_r$-3-14 membered carbocycle substituted with 0-3 R$^a$, or —(CH$_2$)$_r$-5-7 membered heterocycle comprising carbon atoms and 1-4 heteroatoms selected from N, O, and S(O)$_p$ substituted with 0-3 R$^a$;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CH)$_r$-phenyl substituted with 0-3 R$^d$, or —(CH$_2$)$_r$-5-7 membered heterocycle comprising carbon atoms and 1-4 heteroatoms selected from N, O, and S(O)$_p$ substituted with 0-3 R$^d$; or, together with the nitrogen atom to which they are attached, one R$^{11}$ combines with a second R$^{11}$ to form a 4-7 membered heterocycle comprising carbon atoms and 1-4 heteroatoms selected from N, O, and S(O)$_p$ substituted with 0-3 R$^d$;

R$^a$ is, independently at each occurrence, hydrogen, =O, halo, OCF$_3$, CF$_3$, CHF$_2$, CN, NO$_2$, —(CH$_2$)$_r$OR$^b$, —(CH$_2$)$_r$S(O)pR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$ substituted with 0-3 R$^f$; or one R$^a$ together with another R$^a$ located on an adjacent carbon atom can be combined to form a fused ring selected from 3-7 membered cycloalkyl 3-14 membered carbocycle, or 5-7 membered heterocycle comprising carbon atoms and 1-4 heteroatoms selected from N, O, and S(O)$_p$, each ring substituted with 0-3 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CH$_2$)$_r$-5-7 membered heterocycle comprising carbon atoms and 1-4 heteroatoms selected from N, O, and S(O)$_p$ substituted with 0-3 R$^f$, or (CH$_2$)$_r$-6-10 carbocycle substituted with 0-3 R$^d$;

R$^c$ is, independently at each occurrence, C$_{1-6}$ alkyl substituted with 0-3 R$^f$, —(CH$_2$)$_r$—C$_{3-6}$ cycloalkyl substituted with 0-3 R$^f$, or —(CH$_2$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CH$_2$)$_r$C(O)R$^e$, —NR$^e$R$^e$, —NR$^e$C(O)OR$^e$, —C(O)NR$^e$R$^e$, —NR$^e$C(O)R$^e$, —CO$_2$R$^e$, —NR$^e$SO$_2$R$^e$, —SO$_2$R$^e$, C$_{1-6}$ alkyl substituted with 0-3 R$^f$, C$_{3-6}$ cycloalkyl substituted with 0-3 R$^f$, —(CH$_2$)$_r$-phenyl substituted with 0-3 R$^f$ or —(CH$_2$)$_r$-5-7 membered heterocycle comprising carbon atoms and 1-4 heteroatoms selected from N, O, and S(O)$_p$ substituted with 0-3 R$^f$;

R$^e$ is, independently at each occurrence, selected from hydrogen, —C(O)NR$^f$R$^f$, C$_{1-6}$ alkyl, C$_{3-6}$ cycloalkyl, or —(CH$_2$)$_r$-phenyl substituted with 0-3 R$^f$;

R$^f$ is, independently at each occurrence, hydrogen, =O, halo, CN, NH$_2$, NH(C$_{1-6}$alkyl), N(C$_{1-6}$alkyl)$_2$, SO$_2$(C$_{1-6}$alkyl), CO$_2$H, CO$_2$(C$_{1-6}$alkyl), OH, C$_{3-6}$ cycloalkyl, CF$_3$ or O(C$_{1-6}$alkyl);

or R$^f$ is, independently at each occurrence, an optionally substituted —(CH$_2$)$_r$-5-10 membered heterocycle comprising carbon atoms and 1-4 heteroatoms selected from N, O, and S(O)$_p$, phenyl or C$_{3-6}$ cycloalkyl, each group optionally substituted with halo, CN, CF$_3$, C$_{1-6}$ alkyl or O(C$_{1-6}$alkyl);

q, m and n are independently selected from 0, 1, 2 and 3;
p is 0, 1, or 2; and
r is 0, 1, 2, 3, or 4.

In another aspect, there is provided a compound of Formula (I), or stereoisomers, tautomers, pharmaceutically acceptable salts, solvates, or prodrugs thereof, wherein:

R$^1$ is halo, phenyl substituted with 0-3 R$^{1a}$, or C$_{1-6}$ alkyl substituted with 0-3 R$^{1a}$; and R$^{1a}$ is, independently at each occurrence, hydrogen, CF$_3$, halo, C$_{1-6}$ alkyl substituted with 0-3 R$^a$, —(CH$_2$)$_r$OR$^b$, and —(CH$_2$)$_r$-phenyl substituted with 0-3 R$^f$.

In another aspect, there is provided a compound of Formula (I), or stereoisomers, tautomers, pharmaceutically acceptable salts, solvates, or prodrugs thereof, wherein:

R$^2$ is selected from hydrogen, SO$_2$R$^{2c}$, C$_{1-6}$ alkyl substituted with 0-3 R$^{2a}$, pyrimidinyl, CO$_2$R$^{2b}$, —C(O)R$^{2d}$, and —C(O)NR$^{11}$R$^{11}$;

R$^{2a}$ is hydrogen or C$_{1-6}$ alkyl substituted with 0-3 R$^a$;

R$^{2b}$ is hydrogen, C$_{1-6}$ alkyl substituted with 0-3 R$^a$ (Me, Et, tBu), C$_{3-6}$ cycloalkyl substituted with 0-3 R$^a$, —(CH$_2$)$_r$-5-7 membered heterocycle comprising carbon atoms and 1-4 heteroatoms selected from N, O, and S(O)$_p$ substituted with 0-3 R$^a$, or —(CH$_2$)$_r$-phenyl substituted with 0-3 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or a —(CH$_2$)$_r$ 5-10 membered heterocycle containing 1-4 heteroatoms selected from N, O, and S(O)$_p$, substituted with 0-3 R$^a$; and R$^{2d}$ is, independently at each occurrence, hydrogen, C$_{1-6}$ alkyl substituted with 0-3 R$^d$, C$_{1-6}$ haloalkyl, C(O)NR$^{11}$R$^{11}$, C$_{3-6}$ cycloalkyl substituted with 0-2 R$^d$ (Preferably, cycloalkyl is cyclobutyl, cyclohexyl, or cyclopentyl substituted with 0-2 R$^d$), —(CH$_2$)$_r$-phenyl substituted with 0-2 R$^a$, or a 5-10 membered heterocycle containing 1-4 heteroatoms selected from N, O, and S(O)$_p$, substituted with 0-3 R$^a$ (Preferably, the heterocycle is furyl, morpholinyl, piperidinyl, piperazinyl, tetrahydropyranyl, aziridinyl, pyrolidinyl, pyridyl, or benzoisothiazolyl, each substituted with 0-3 R$^a$).

In another aspect, there is provided a compound of Formula (I), or stereoisomers, tautomers, pharmaceutically acceptable salts, solvates, or prodrugs thereof, wherein:

R$^3$ is hydrogen, halo, N$_3$, CN, OR$^{3b}$, —NH$_2$, NH(C$_{1-6}$ alkyl), N(C$_{1-6}$ alkyl)$_2$, C$_{1-6}$ alkyl substituted with 0-3 R$^{3a}$ or C$_{3-10}$ cycloalkyl substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CH$_2$)$_r$OR$^b$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CH$_2$)$_r$-3-14 membered carbocycle substituted with 0-3 R$^a$, or a —(CH$_2$)$_r$-5-10 membered heterocycle comprising carbon atoms and 1-4 heteroatoms selected from N, O, and S(O)$_p$ substituted with 0-3 R$^a$; and R$^{3b}$ is, independently at each occurrence, hydrogen, C$_{1-6}$ alkyl substituted with 0-3 R$^a$ or phenyl substituted with 0-3 R$^a$.

In another aspect, there is provided a compound having the following formula:

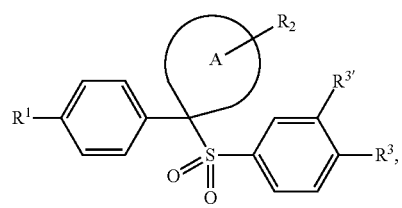

or a stereoisomer or pharmaceutically-acceptable salt thereof, wherein:

A is a 3-7 membered heterocycle comprising carbon atoms, and 1-4 heteroatoms selected from N, O, and $S(O)_p$;

$R^1$ is halo, phenyl substituted with 0-3 $R^{1a}$, or $C_{1-6}$ alkyl substituted with 0-3 $R^a$;

$R^{1a}$ is, independently at each occurrence, hydrogen, $CF_3$, halo, $C_{1-6}$ alkyl substituted with 0-3 $R^a$, $-(CH_2)_rOR^b$, and $-(CH_2)_r$-phenyl substituted with 0-3 $R^a$;

$R^2$ is selected from hydrogen, $SO_2R^{2c}$, $C_{1-6}$ alkyl substituted with 0-3 $R^{2a}$, pyrimidinyl, $CO_2R^{2b}$, $-C(O)R^{2d}$, and $-C(O)NR^{11}R^{11}$;

$R^{2a}$ is hydrogen or $C_{1-6}$ alkyl substituted with 0-3 $R^a$;

$R^{2b}$ is hydrogen, $C_{1-6}$ alkyl substituted with 0-3 $R^a$, $C_{3-6}$ cycloalkyl substituted with 0-3 $R^a$, $-(CH_2)_r$-5-7 membered heterocycle comprising carbon atoms and 1-4 heteroatoms selected from N, O, and $S(O)_p$ substituted with 0-3 $R^a$, or $-(CH_2)_r$-phenyl substituted with 0-3 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or a $-(CH_2)_r$ 5-10 membered heterocycle containing 1-4 heteroatoms selected from N, O, and $S(O)_p$, substituted with 0-3 $R^a$;

$R^{2d}$ is, independently at each occurrence, hydrogen, $C_{1-6}$ alkyl substituted with 0-3 $R^d$ (Me), $C_{1-6}$ haloalkyl, $C(O)NR^{11}R^{11}$, $C_{3-6}$ cycloalkyl substituted with 0-2 $R^d$, $(CH_2)_r$-phenyl substituted with 0-2 $R^a$, or a 5-10 membered heterocycle containing 1-4 heteroatoms selected from N, O, and $S(O)_p$, substituted with 0-3 $R^a$;

$R^3$ and $R^{3'}$ are, independently, hydrogen, halo, $N_3$, CN, $OR^{3b}$, $-NH_2$, $NH(C_{1-6}$ alkyl), $N(C_{1-6}$ alkyl$)_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, $-(CH_2)_rOR^b$, $-(CH_2)_rS(O)_pR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $-(CH_2)_r$-3-14 membered carbocycle substituted with 0-3 $R^a$, or a $-(CH_2)_r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $C_{1-6}$ alkyl substituted with 0-3 $R^a$ or phenyl substituted with 0-3 $R^a$;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, $-(CH_2)_r$-phenyl substituted with 0-3 $R^d$, or $-(CH_2)_r$-5-7 membered heterocycle comprising carbon atoms and 1-4 heteroatoms selected from N, O, and $S(O)_p$ substituted with 0-3 $R^d$; or, together with the nitrogen atom to which they are attached, one $R^{11}$ combines with a second $R^{11}$ to form a 4-7 membered heterocycle comprising carbon atoms and 1-4 heteroatoms selected from N, O, and $S(O)_p$ substituted with 0-3 $R^d$;

$R^a$ is, independently at each occurrence, hydrogen, =O, halo, $OCF_3$, $CF_3$, $CHF_2$, CN, $NO_2$, $-(CH_2)_rOR^b$, $-(CH_2)_rS(O)pR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, $-(CH_2)_r$-3-14 membered carbocycle, or $-(CH_2)_r$-5-7 membered heterocycle comprising carbon atoms and 1-4 heteroatoms selected from N, O, and $S(O)_p$ substituted with 0-3 $R^f$; or one $R^a$ together with another $R^a$ located on an adjacent carbon atom can be combined to form a fused ring selected from 3-7 membered cycloalkyl 3-14 membered carbocycle, or 5-7 membered heterocycle comprising carbon atoms and 1-4 heteroatoms selected from N, O, and $S(O)_p$, each ring substituted with 0-3 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, $-(CH_2)_r$-5-7 membered heterocycle comprising carbon atoms and 1-4 heteroatoms selected from N, O, and $S(O)_p$ substituted with 0-3 $R^f$, or $-(CH_2)_r$-6-10 carbocycle substituted with 0-3 $R^d$;

$R^c$ is, independently at each occurrence, $C_{1-6}$ alkyl substituted with 0-3 $R^f$, $-(CH_2)_r$-$C_{3-6}$ cycloalkyl substituted with 0-3 $R^f$, $-(CH_2)_r$-phenyl substituted with 0-3 $R^f$, or $R^d$ is, independently at each occurrence, hydrogen, =O, halo, $OCF_3$, $CF_3$, CN, $NO_2$, $-OR^e$, $-(CH_2)_rC(O)R^c$, $-NR^eR^e$, $-NR^eC(O)OR^c$, $-C(O)NR^eR^e$, $-NR^eC(O)R^c$, $CO_2R^c$, $-NR^eSO_2R^c$, $SO_2R^c$, $C_{1-6}$ alkyl substituted with 0-3 $R^f$, $C_{3-6}$ cycloalkyl substituted with 0-3 $R^f$, $-(CH_2)_r$-phenyl substituted with 0-3 $R^f$, or $-(CH_2)_r$-5-7 membered heterocycle comprising carbon atoms and 1-4 heteroatoms selected from N, O, and $S(O)_p$ substituted with 0-3 $R^f$;

$R^e$ is, independently at each occurrence, selected from hydrogen, $C(O)NR^fR^f$, $C_{1-6}$ alkyl, $C_{3-6}$ cycloalkyl, and $(CH_2)_r$-phenyl substituted with 0-3 $R^f$;

$R^f$ is, independently at each occurrence, hydrogen, =O, halo, CN, $NH_2$, $NH(C_{1-6}$alkyl), $N(C_{1-6}$alkyl$)_2$, $SO_2(C_{1-6}$ alkyl), $CO_2H$, $CO_2(C_{1-6}$alkyl), OH, $C_{3-6}$ cycloalkyl, $CF_3$ or $O(C_{1-6}$alkyl);

or $R^f$ is, independently at each occurrence, an optionally substituted $-(CH_2)_r$-5-10 membered heteroaryl comprising carbon atoms and 1-4 heteroatoms selected from N, O, and S, phenyl or $C_{3-6}$ cycloalkyl, each group optionally substituted with halo, CN, $CF_3$, $C_{1-6}$ alkyl or $O(C_{1-6}$ alkyl);

In another aspect, there is provided a compound of Formula (I), or stereoisomers, tautomers, pharmaceutically acceptable salts, solvates, or prodrugs thereof, wherein A is tetrahydropyranyl.

In another aspect, there is provided a compound of Formula (I), or stereoisomers, tautomers, pharmaceutically acceptable salts, solvates, or prodrugs thereof, wherein A is piperidinyl.

In another aspect, there is provided a compound of Formula (I), or stereoisomers, tautomers, pharmaceutically acceptable salts, solvates, or prodrugs thereof, A is

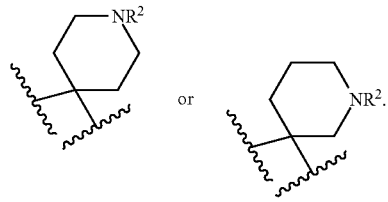

In another aspect, there is provided a compound of Formula (I), or stereoisomers, tautomers, pharmaceutically acceptable salts, solvates, or prodrugs thereof, wherein $R^1$ is Preferably R¹ is

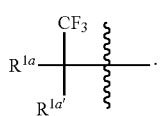

In another aspect, there is provided a compound of Formula (I), or stereoisomers, tautomers, pharmaceutically acceptable salts, solvates, or prodrugs thereof, wherein R¹ is

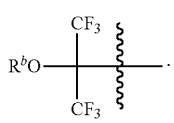  or

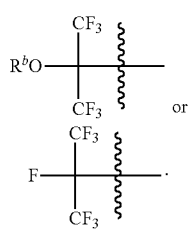

Preferably R¹ is

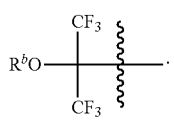

In another aspect, there is provided a compound of Formula (I), or stereoisomers, tautomers, pharmaceutically acceptable salts, solvates, or prodrugs thereof, wherein R² is $CO_2R^{2b}$, —C(O)R$^{2d}$, or C(O)NR$^{11}$R$^{11}$.

In another aspect, there is provided a compound of Formula (I), or stereoisomers, tautomers, pharmaceutically acceptable salts, solvates, or prodrugs thereof, wherein R³ and R³' are, independently, hydrogen, halo, N₃, CN, —O(phenyl), —NH₂, NH($C_{1-6}$ alkyl), N($C_{1-6}$ alkyl)₂, $C_{1-6}$ alkyl or $C_{3-6}$ cycloalkyl. Preferably, R³ is F, H, OMe, NH₂, N₃, CN, OPh, cyclopropyl, or CH₃, and R³' is hydrogen. More preferably R³ is F and R³' is hydrogen.

In another aspect, there is provided a compound of Formula (I) having the following formula:

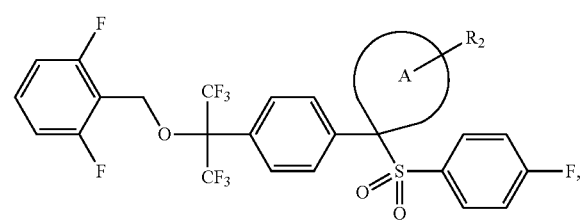

or a stereoisomer or pharmaceutically-acceptable salt thereof.

In another aspect, there is provided a compound of Formula (I), or stereoisomers, tautomers, pharmaceutically acceptable salts, solvates, or prodrugs thereof, wherein R² is: H, I

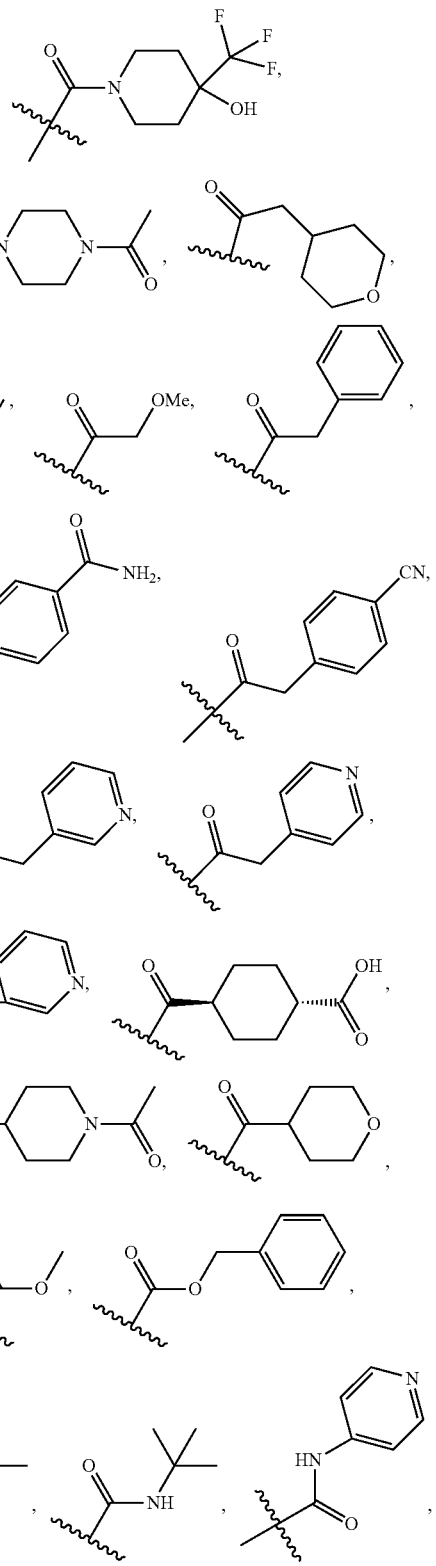

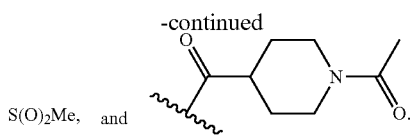

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a compound of the present invention for use in treating diseases (or a method of treating diseases) in which inflammation is a component including, without limitation, diseases such as psoriasis, rheumatoid arthritis, inflammatory bowel disease, Crohn's disease, ulcerative colitis, acute graft-versus-host disease, psoriatic arthritis, ankylosing spondylitis and multiple sclerosis.

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

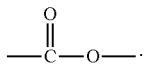

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2$H, or S(O)H group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

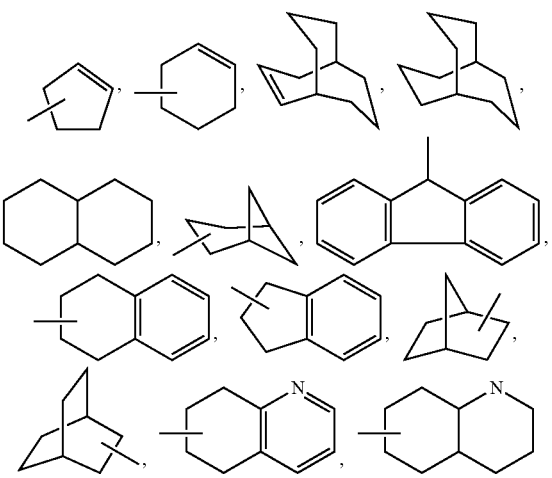

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, di, and trifluoromethyl.

The term "haloalkoxy" means an alkoxy group having one or more halo substituents. For example, "haloalkoxy" includes $OCF_3$.

Thus, examples of aryl groups include:

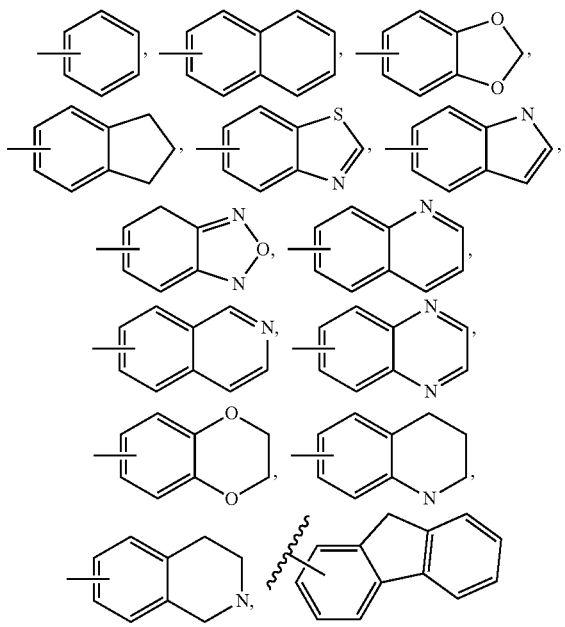

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocycle groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

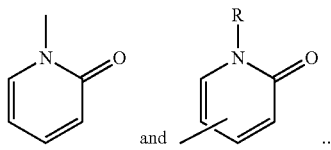

and

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include

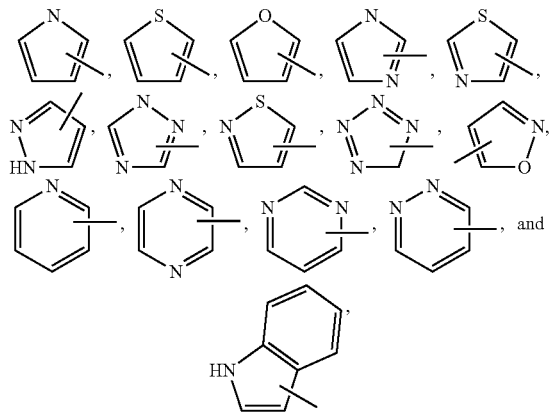

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The terms "carbocycle, carbocyclyl or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and c) Bundgaard, H., *Adv. Drug Deliv. Rev.,* 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Another aspect of the invention is a pharmaceutical composition including a compound, stereoisomeric form, pharmaceutical salt, solvate or hydrate as described herein. The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention are useful to prevent, diagnose, and treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to formula (I), stereoisomeric form, N-oxide, pharmaceutically acceptable salt, solvate, hydrate or pharmaceutical composition as described herein. See, e.g., L. A. Solt et al., "Action of RORs and their ligands in (patho)physiology," *Trends Endocrinol Metab.*, preprint available online Jul. 11, 2012 at http://www.sciencedirect.com/science/article/pii/S1043276012000926; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," *Nat. Immunol.*, 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," *Inflamm. Allergy Drug Targets,* 2012 April; 11(2): 159-68, which is hereby incorporated herein by reference in its entirety, as well as the references discussed in the Background section.

In other embodiments, the disease or disorder is inflammatory bowel disease. See, e.g., M. Leppkes et al., "RORgamma-expressing Th17 cells induce murine chronic intestinal inflammation via redundant effects of IL-17A and IL-17F," *Gastroenterology,* 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the CD2 promoter induces polyclonal plasmacytosis and autoantibody production in transgenic mice," *Eur. J. Immunol.,* 2012 August; 42(8): 1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," *J. Clin. Invest.,* 2012 Jun. 1; 122(6):2252-6; and S. P. Raychaudhuri, "Role of IL-17 in Psoriasis and Psoriatic Arthritis," Clin. Rev. Allergy Immunol., preprint available online Feb. 24, 2012 at http://rd.springer.com/article/10.1007/s12016-012-8307-1 (PubMed PMID: 22362575), each of which is hereby incorporated herein by reference in its entirety, as well as the references discussed in the Background section.

In other embodiments, the disease or disorder is psoriatic arthritis. See, e.g., S. P. Raychaudhuri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factorT-bet and RORγt in mice," *Blood,* 2011 Nov. 3; 118(18):5011-20, which is hereby incorporated herein by reference in its entirety, as well as the references discussed in the Background section.

In other embodiments, the disease or disorder is autoimmune uveitis. See, e.g., R. Horai et al., "Cytokines in autoimmune uveitis," *J. Interferon Cytokine Res.,* 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," *EMBO Mol. Med.,* 2011 November; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. Nat. Med., 2012 July; 18:1248-53, which is hereby incorporated herein by reference in its entirety, as well as the references discussed in the Background section.

In certain aspects, the medical disorder being diagnosed, treated, or prevented by use of the presently disclosed compounds can be, for example, an autoimmune disorder. In other embodiments, the disorder being diagnosed, treated or prevented by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

Scheme 1 illustrates a general synthesis of piperidine 10. Appropriately functionalized benzyl halide 1 can be reacted with functionalized thiophenol 2 using a base such as potassium carbonate or sodium hydroxide in a solvent such as tetrahydrofuran, ethanol or N,N-dimethylformamide to provide sulfide intermediate 3. Oxidation of 3 to sulfone 4 can be accomplished with mCPBA or other oxidant such as oxone and sodium tungstate. Alternatively, sulfone 4 can be synthesized in one step by treating 1 with sodium benzenesulfinate 5 in a solvent such as N,N-dimethylformamide. Upon treatment with n-butyllithium, the resulting anion derivative of 4 can be reacted with Eschenmoser's salt (dimethylmethylideneammonium iodide) to yield amine derivative 6, which can be converted to vinyl sulfone 7 after heating in acetic anhydride and toluene. Vinyl sulfone 7 can also be synthesized directly from 4 by heating with N,N,N',N'-tetramethylmethylenediamine and acetic anhydride in N,N-dimethylformamide. Michael addition of 3-aminopropanol to vinyl sulfone 7 can provide alcohol 8. After reaction with methanesulfonyl chloride and a base such as triethylamine, the resulting mesylate 9 can be converted to piperidine 10 using a base such as potassium t-butoxide or sodium hydride. The two enantiomers of 10 can be resolved with chiral HPLC. Racemic or enantiomerically pure form of 10 can be further functionalized following conditions described in Scheme 3 below.

Scheme 1

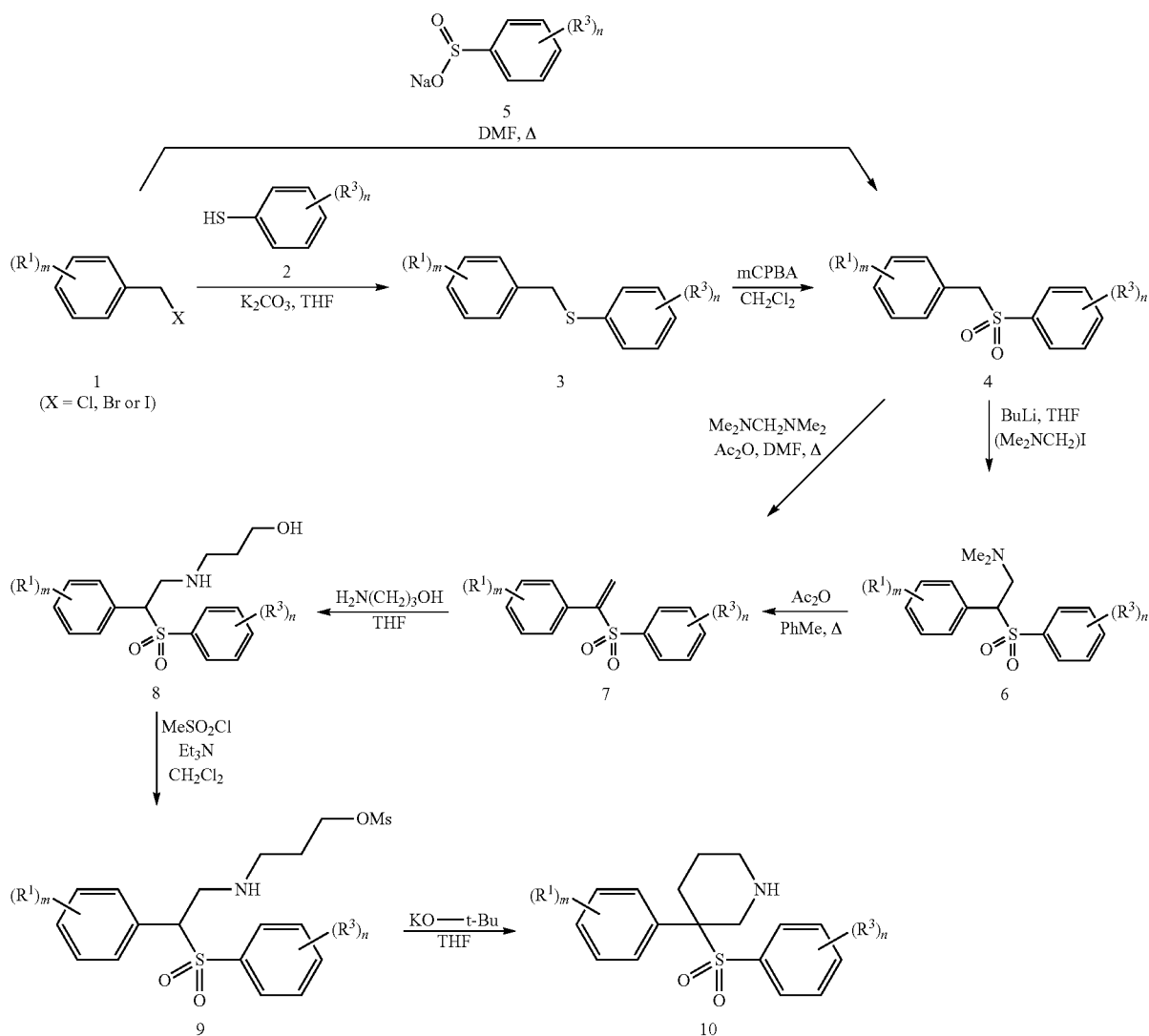

Scheme 2 illustrates a synthesis of a series of compounds 17 and 18 where $R^1$ is 1,1,1,3,3,3-hexafluoro-2-hydroxypropan-2-yl group. Commercially available 1,1,1,3,3,3-hexafluoro-2-(p-tolyl)propan-2-ol (11) can be selectively brominated with N-bromosuccinimide in refluxing carbon tetrachloride using AIBN as radical initiator to yield bromide 12. Reaction of 12 with sodium benzenesulfinate 5 in a solvent such as N,N-dimethylformamide could lead to sulfone product 13. The hydroxyl group in 13 can be protected as a benzyl ether using conditions such as benzyl bromide and potassium carbonate in N,N-dimethylformamide. Treatment of the resulting benzyl ether 14 with di-halide 15 in a solvent such as N,N-dimethylformamide under basic conditions (such as sodium hydride) can provide tetrahydropyran 16a and piperidine 16b. Palladium(II) hydroxide-catalyzed hydrogenolysis of 16 could cleave the benzyl ether to provide the two alcohol products 17a and 17b. The Boc protecting group in 17b can be removed with trifluoroacetic acid or hydrogen chloride to yield piperidine 18, which can be further functionalized according to conditions outlined in Scheme 3.

Scheme 2

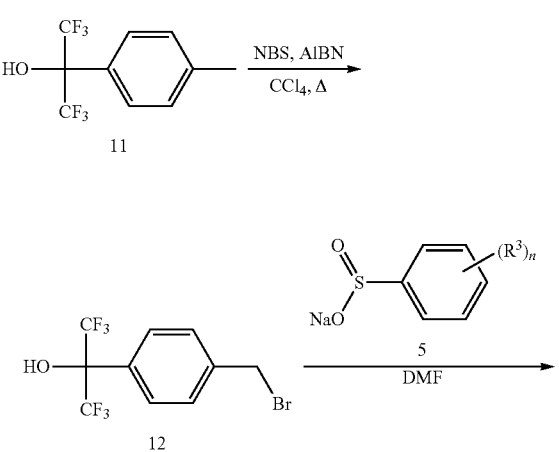

-continued

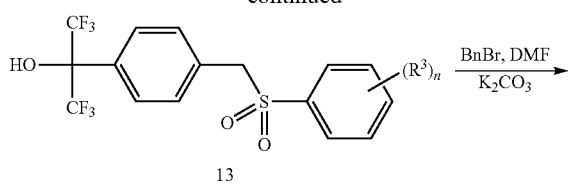

13

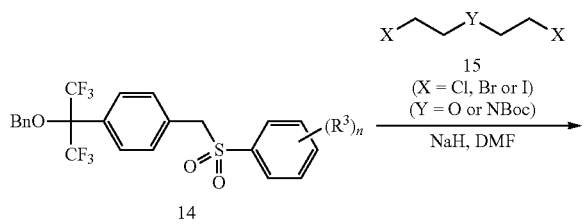

14

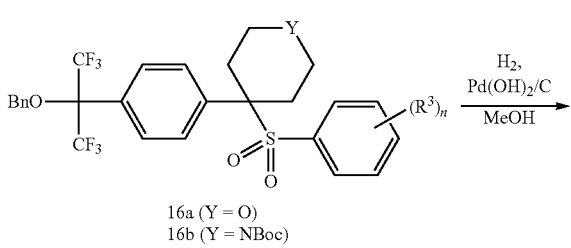

16a (Y = O)
16b (Y = NBoc)

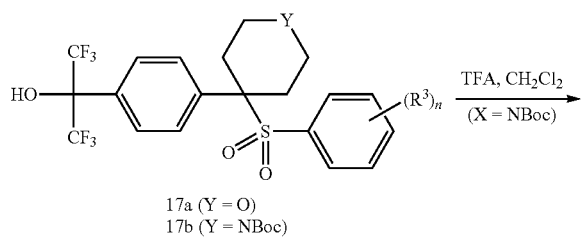

17a (Y = O)
17b (Y = NBoc)

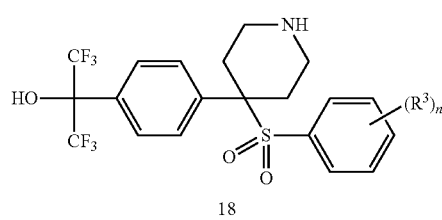

18

The free cyclic amines of compound 19 (for example, 3-piperidinyl analogue 10 and 4-piperidinyl analogue 18) can be functionalized using various well known transformations to give 20 (Scheme 3). Examples of these transformations include, but are not limited to, alkylation reaction with alkyl halide and a base such as Hunig's base, reductive alkylation with aldehyde/ketone and a reducing reagent such as sodium triacetoxyborohydride, coupling reaction with carboxylic acid using an activating agent such as BOP or HOBt/EDC, and other acylation reactions using acid chloride, anhydride, chloroformate, isocyanate, and sulfonyl chloride. Optionally, enantiomers of 20 can be separated using chiral HPLC if racemic 19 is used in the reaction.

Scheme 3

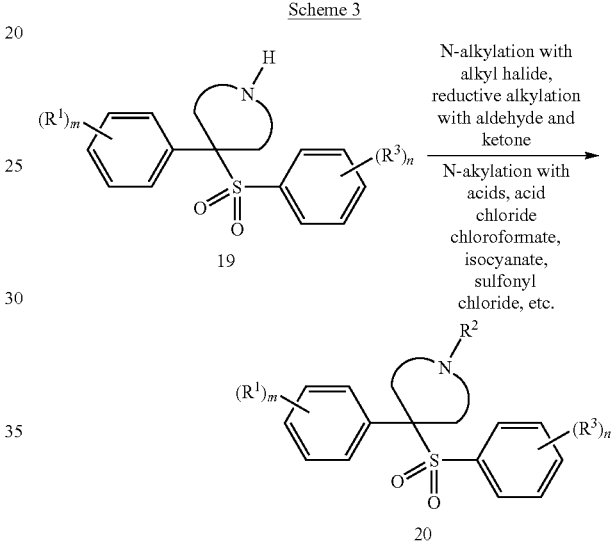

Compound 21, prepared according to Schemes 1-3, can also be useful intermediate for further derivatization (Scheme 4). For example, it can be alkylated with $R^{1a}$-halide (chloride, bromide or iodide) under basic conditions such as potassium carbonate or sodium hydride to give 22. Alternatively, compound 22 can be synthesized from 21 and alcohol $R^{1a}$—OH using Mitsunobu conditions involving an azodicarboxylate such as diethyl azodicarboxylate (DEAD) and a phosphine ligand such as triphenylphosphine or tributylphosphine. The hydroxyl group in 21 can also be replaced with a fluoro group using (diethylamino)sulfur trifluoride (DAST) to give perfluoroisopropyl analogue 23. In addition, the OH group in 21 can be arylated with diphenyliodonium iodide 24 using a base such as potassium methoxide or sodium hydride to give phenyl ether 25. All of the transformation in Scheme 4 can also be carried out on suitably protected cyclic amine 21 ($R^2$=protecting group such as Bn, Boc or Cbz). Subsequent deprotection and chemical manipulation to install $R^2$ group would complete the synthesis.

Scheme 4

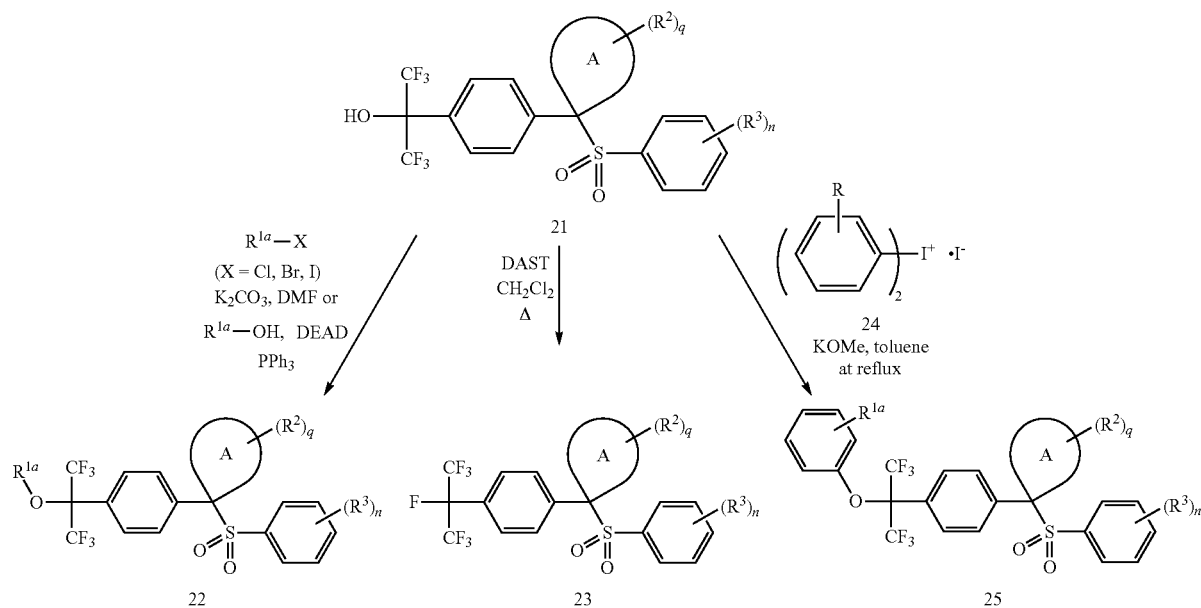

Iodide 26, prepared from the sequence outlined in Scheme 1, can be a useful intermediate for further diversification to prepare 28, 30 and 31 (Scheme 5). It can be reacted with aryl/heteroaryl boronic acid (or ester) 27 under well-known Suzuki coupling conditions using a catalyst such as palladium tetrakis(triphenylphosphine) or Pd(dppf)Cl$_2$ to give compound 28. Compound 28 can also be obtained under Stille coupling conditions using aryl/heteroaryltin in place of the boronic acid 27. Iodide 26 can also be treated with tert-butyllithium or ethylmagensium bromide to produce the corresponding aryllithium or arylmagnesium species, which can react with ketone 29 to produce alcohol 30. Compound 30 can in turn be converted to ether 31 using previously described conditions. All of the transformations in Scheme 5 can also be performed on suitably protected cyclic amine 26 ($R^2$=protecting group such as Bn, Boc or Cbz). Subsequent deprotection and chemical manipulation to install $R^2$ group would complete the synthesis.

Scheme 5

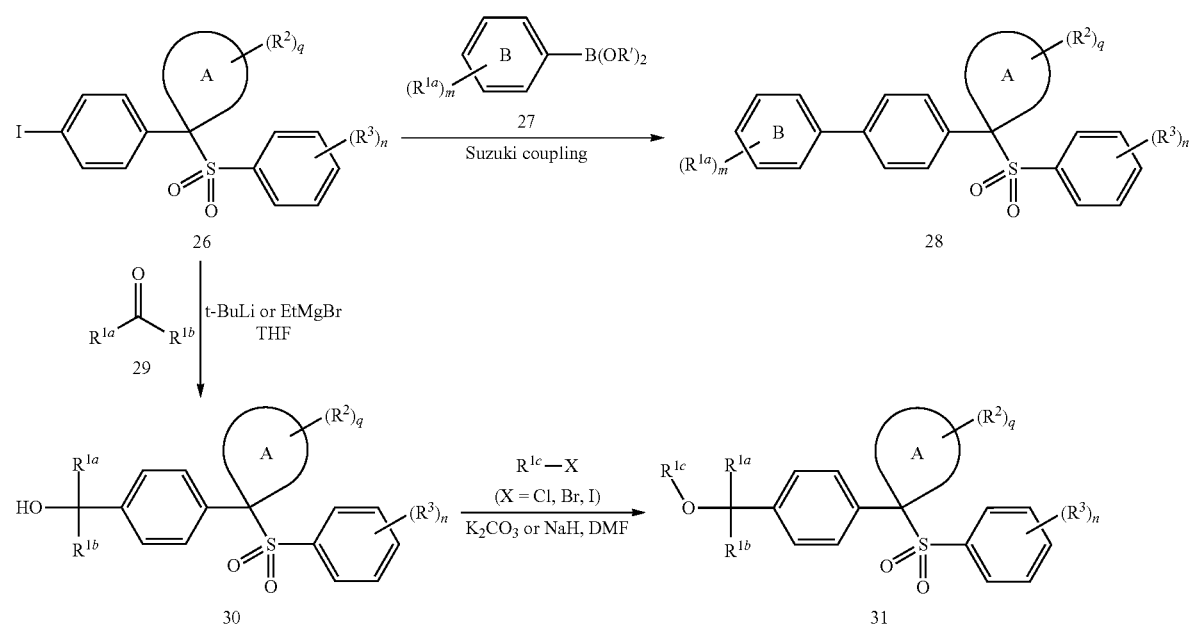

B = aryl of heteroaryl

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

HPLC Conditions

Condition A:
Column: YMC Combiscreen ODS-A 4.6×50 mm (4 min.); Linear gradient of 0 to 100% solvent B over 4 min with 1 min hold at 100% B; UV visualization at 220 nm; Solvent A=10% MeOH, 90% $H_2O$, 0.2% $H_3PO_4$; Solvent B=90% MeOH, 10% $H_2O$, 0.2% $H_3PO_4$; Flow: 4 mL/min.

Condition B:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Condition C:
Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Condition D:
Column: XBridge Phenyl, 4.6×150 mm, 3.5 micron; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 1 mL/min.

Condition E:
Column: ZORBAX CN, 4.6×150 mm, 5 micron; Mobile Phase A: 5:95 acetonitrile:water with 10 mM ammonium acetate; Mobile Phase B: 95:5 acetonitrile:water with 10 mM ammonium acetate; Gradient: 10-100% B over 25 minutes, then a 5-minute hold at 100% B; Flow: 1 mL/min.

Condition F:
Column: SUNFIRE C18, 4.6×150 mm, 3.5 micron; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 1 mL/min.

Condition G:
Column: Ascentis Express C18 (4.6×50) mm, 2.7 μm; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 4 minutes; Flow: 4.00 mL/min.

Condition H:
Column: Ascentis Express C18 (2.1×50) mm, 2.7 μm; Mobile Phase A: 5:95 acetonitrile:water with 10 mM ammonium acetate; Mobile Phase B: 95:5 acetonitrile:water with 10 mM ammonium acetate; Gradient: 0-100% B over 3.4 minutes; Flow: 1.11 mL/min.

Example 1

4-(4-(2-((2,6-difluorobenzyl)oxy)-1,1,1,3,3,3-hexafluoropropan-2-yl)phenyl)-4-((4-fluorophenyl)sulfonyl)tetrahydro-2H-pyran Step A: 2-(4-(bromomethyl)phenyl)-1,1,1,3,3,3-hexafluoropropan-2-ol

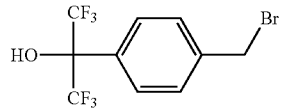

N-Bromosuccinimide (13.79 g, 77 mmol) and 2,2'-azobis(2-methylpropionitrile) (0.025 g, 0.155 mmol) were added to a solution of 1,1,1,3,3,3-hexafluoro-2-(p-tolyl)propan-2-ol (20.00 g, 77 mmol) in carbon tetrachloride (80 mL). The resulting suspension was heated to reflux under nitrogen for 4 h, cooled to room temperature and filtered through celite. The filter cake was rinsed with ether. The filtrate was concentrated under reduced pressure. The residue was treated with ether (100 mL) and hexanes (50 mL), stirred for 15 min and filtered. The filtrate was concentrated under reduced pressure and dried under vacuum to give crude product as tan liquid (27.07 g). 1H NMR analysis showed a 69:15:16 molar ratio of the desired 2-(4-(bromomethyl)phenyl)-1,1,1,3,3,3-hexafluoropropan-2-ol, unreacted 1,1,1,3,3,3-hexafluoro-2-(p-tolyl)propan-2-ol and 2-(4-(dibromomethyl)phenyl)-1,1,1,3,3,3-hexafluoropropan-2-ol. The mixture was used without further purification, assuming ~70% purity of the desired 2-(4-(bromomethyl)phenyl)-1,1,1,3,3,3-hexafluoropropan-2-ol.

Step B: 1,1,1,3,3,3-hexafluoro-2-(4-((phenylsulfonyl)methyl)phenyl)propan-2-ol

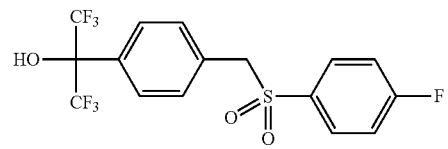 [SMILES: O=S(=O)(Cc1ccc(C(O)(C(F)(F)F)C(F)(F)F)cc1)c1ccc(F)cc1]

Sodium 4-fluorobenzenesulfinate (12.62 g, 69.3 mmol) was added in small portions to a stirred solution of 2-(4-(bromomethyl)phenyl)-1,1,1,3,3,3-hexafluoropropan-2-ol (20.00 g, ~70% pure from Step A) in N,N-dimethylformamide (80 mL). The mixture warmed up slightly during the addition. After 6 h at ambient temperature, the mixture was diluted with ethyl acetate (1 L), washed with water (3×200 mL), brine (100 mL), dried (magnesium sulfate), filtered and concentrated under reduced pressure. The residue was dissolved in dichloromethane (40 mL), triturated with hexanes (400 mL), stirred for 30 min and filtered. The filter cake was washed with hexanes (100 mL) and dried under vacuum to give 1,1,1,3,3,3-hexafluoro-2-(4-((phenylsulfonyl)methyl)phenyl)propan-2-ol as white solid (14.84 g, 82% yield). LC/MS (M+23): 439.2; 1H NMR (400 MHz, CDCl$_3$) δ ppm 7.64 (d, J=8.1 Hz, 2H), 7.62-7.54 (m, 2H), 7.20 (d, J=8.6 Hz, 2H), 7.15-7.06 (m, 2H), 4.34 (s, 2H), 3.59 (s, 1H).

Step C: 1,3-difluoro-2-(((1,1,1,3,3,3-hexafluoro-2-(4-(((4-fluorophenyl)sulfonyl)methyl)phenyl)propan-2-yl)oxy)methyl)benzene

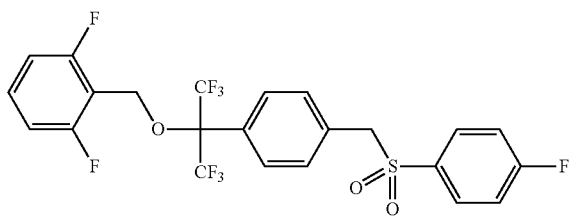 [SMILES: O=S(=O)(Cc1ccc(C(OCc2c(F)cccc2F)(C(F)(F)F)C(F)(F)F)cc1)c1ccc(F)cc1]

A mixture of 1,1,1,3,3,3-hexafluoro-2-(4-(((4-fluorophenyl)sulfonyl)methyl)phenyl)propan-2-ol (12.625 g, 30.3 mmol), 2-(bromomethyl)-1,3-difluorobenzene (6.59 g, 31.8 mmol) and potassium carbonate (12.57 g, 91 mmol) in N,N-dimethylformamide (120 mL) was stirred under nitrogen at room temperature for 22 h. The mixture was quenched with saturated ammonium chloride (100 mL), diluted with ethyl acetate (800 mL), washed with water (3×100 mL), brine (50 mL), dried (magnesium sulfate), filtered and concentrated under reduced pressure. The residue was treated with dichloromethane (20 mL) and toluene (40 mL), sonicated, triturated with hexanes (500 mL), stirred for 15 min and filtered. The filter cake was washed with hexanes (100 mL) and dried under vacuum to give first batch of 1,3-difluoro-2-(((1,1,1,3,3,3-hexafluoro-2-(4-(((4-fluorophenyl)sulfonyl)methyl)phenyl)propan-2-yl)oxy)methyl)benzene as white solid (14.881 g). The filtrate was concentrated. Silica gel chromatography, eluting with 5-30% ethyl acetate in hexanes, gave second batch of the desired product as white solid (0.735 g). The combined amount of the product is 15.616 g (95% yield). LC/MS (M+18): 560.2; LC retention time: 4.460 min (analytical HPLC Method A); 1H NMR (400 MHz, CDCl$_3$) δ ppm 7.68-7.57 (m, 4H), 7.37 (tt, J=8.4, 6.4 Hz, 1H), 7.28-7.21 (m, 2H), 7.15-7.07 (m, 2H), 7.01-6.91 (m, 2H), 4.68 (s, 2H), 4.36 (s, 2H).

Step D: 4-(4-(2-((2,6-difluorobenzyl)oxy)-1,1,1,3,3,3-hexafluoropropan-2-yl)phenyl)-4-((4-fluorophenyl)sulfonyl)tetrahydro-2H-pyran

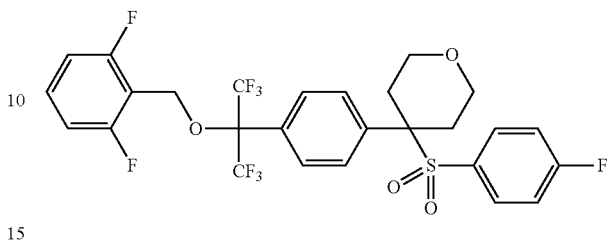

Sodium hydride (13.27 mg, 0.332 mmol, 60% suspension in mineral oil) was added to a solution of 1,3-difluoro-2-(((1,1,1,3,3,3-hexafluoro-2-(4-(((4-fluorophenyl)sulfonyl)methyl)phenyl)propan-2-yl)oxy)methyl)benzene (18 mg, 0.033 mmol) and 1-iodo-2-(2-iodoethoxy)ethane (32.4 mg, 0.100 mmol) in N,N-dimethylformamide (1 mL). After 1 h at room temperature, the reaction was complete as judged by LCMS analysis. The mixture was quenched with saturated ammonium chloride (1 mL), diluted with ethyl acetate (20 mL), washed with water (2×5 mL), brine (5 mL), dried (magnesium sulfate), filtered and concentrated under reduced pressure. Silica gel chromatography, eluting with 5-40% ethyl acetate in hexanes, gave Example 1 as white solid (17.4 mg, 81% yield). LC/MS (M+18): 630.1; LC retention time: 4.541 min (analytical HPLC Method A); 1H NMR (400 MHz, CDCl$_3$) δ ppm 7.63 (d, J=8.4 Hz, 2H), 7.44-7.31 (m, 3H), 7.28-7.19 (m, 2H), 7.03-6.89 (m, 4H), 4.73 (s, 2H), 4.07-3.96 (m, J=11.8, 1.7 Hz, 2H), 3.37 (t, J=11.2 Hz, 2H), 2.77-2.62 (m, 2H), 2.45 (d, J=12.3 Hz, 2H).

Example 2

(3-(4-(2-((2,6-difluorobenzyl)oxy)-1,1,1,3,3,3-hexafluoropropan-2-yl)phenyl)-3-((4-fluorophenyl)sulfonyl)piperidin-1-yl)(4-hydroxy-4-(trifluoromethyl)piperidin-1-yl)methanone Step A: 1,3-difluoro-2-(((1,1,1,3,3,3-hexafluoro-2-(4-(1-((4-fluorophenyl)sulfonyl)vinyl)phenyl)propan-2-yl)oxy)methyl)benzene

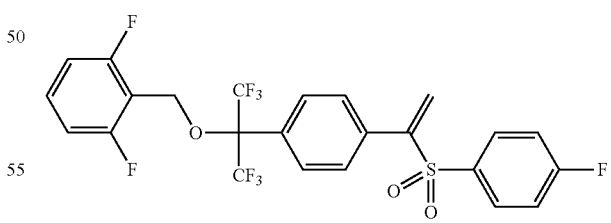

Acetic anhydride (10.35 mL, 110 mmol) was added to a solution of 1,3-difluoro-2-(((1,1,1,3,3,3-hexafluoro-2-(4-(((4-fluorophenyl)sulfonyl)methyl)phenyl)propan-2-yl)oxy)methyl)benzene (14.88 g, 27.4 mmol, from Step C of Example 1) and N,N,N',N'-tetramethylmethanediamine (14.97 mL, 110 mmol) in N,N-dimethylformamide (140 mL) at room temperature. The reaction flask was equipped with a condenser, placed in a 60° C. oil bath and stirred under nitrogen for 5 h. Additional N,N,N',N'-tetramethylmethanediamine (14.97 mL, 110 mmol) and acetic anhydride (10.35 mL, 110 mmol) were added dropwise and the mixture stirred at 60° C. for 15 h. Additional acetic anhydride (5 mL) was added. After 1 h at 60° C., the mixture was diluted with ethyl acetate (1.2 L), washed with saturated sodium bicarbonate (3×200 mL), water (200 mL), brine (200 mL), dried (magnesium sulfate), filtered and concentrated under reduced pressure. Silica gel chromatography, eluting with 5-25% ethyl acetate in hexanes, gave impure 1,3-difluoro-2-(((1,1,1,3,3,3-hexafluoro-2-(4-(1-((4-fluorophenyl)sulfonyl)vinyl)phenyl)propan-2-yl)oxy)methyl)benzene as tan solid (8.834 g). This material was taken to the next reaction without further purification.

Step B: 3-((2-(4-(2-((2,6-difluorobenzyl)oxy)-1,1,1,3,3,3-hexafluoropropan-2-yl)phenyl)-2-((4-fluorophenyl)sulfonyl)ethyl)amino)propan-1-ol

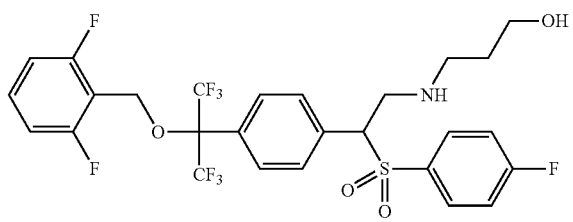 [SMILES: O=S(=O)(c1ccc(F)cc1)C(CNCCCO)c1ccc(C(OCc2c(F)cccc2F)(C(F)(F)F)C(F)(F)F)cc1]

In a 25 mL dry round bottom flask under nitrogen atmosphere, a solution of 1,3-difluoro-2-(((1,1,1,3,3,3-hexafluoro-2-(4-(1-((4-fluorophenyl)sulfonyl) vinyl)phenyl)propan-2-yl)oxy)methyl)benzene (20 mg, 0.036 mmol) and 3-aminopropan-1-ol (3.25 mg, 0.043 mmol) in anhydrous tetrahydrofuran (2 mL) was stirred at 25° C. for 12 h. After evaporation of tetrahydrofuran under reduced pressure, the residue was purified by Prep-HPLC to give 3-((2-(4-(2-((2,6-difluorobenzyl)oxy)-1,1,1,3,3,3-hexafluoropropan-2-yl)phenyl)-2-((4-fluorophenyl)sulfonyl)ethyl)amino)propan-1-ol as white solid (9.23 mg, 41% yield). LC/MS (M+1): 630.7; LC retention time: 13.30 min (analytical HPLC Method F); 1H NMR (DMSO-d6, 400 MHz): δ ppm 7.65-7.50 (m, 5H), 7.46 (d, J=8.40 Hz, 2H), 7.34 (t, J=8.8 Hz, 2H), 7.22 (t, J=8.0 Hz, 2H), 4.87 (q, J=4.8 Hz, 1H), 4.61 (q, J=10 Hz, 2H), 4.30-4.28 (m, 1H), 3.43-3.19 (m, 3H), 2.60-2.45 (m, 2H), 1.65 (br-S, 1H), 1.43 (t, J=6.4 Hz, 2H); 19F NMR (376 MHz): δ −70.01, −104.69, −115.03.

Step C: 3-((2-(4-(2-((2,6-difluorobenzyl)oxy)-1,1,1,3,3,3-hexafluoropropan-2-yl)phenyl)-2-((4-fluorophenyl)sulfonyl)ethyl)amino)propyl methanesulfonate

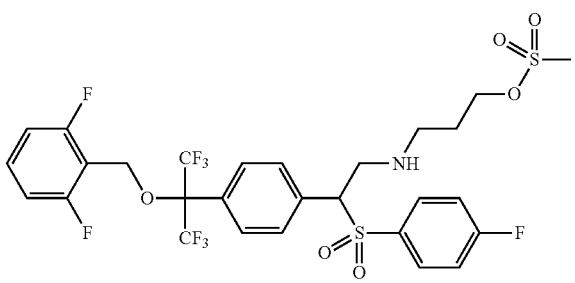 [SMILES: CS(=O)(=O)OCCCNCC(c1ccc(C(OCc2c(F)cccc2F)(C(F)(F)F)C(F)(F)F)cc1)S(=O)(=O)c1ccc(F)cc1]

In a 100 mL round bottom flask, a solution of 3-((2-(4-(2-((2,6-difluorobenzyl)oxy)-1,1,1,3,3,3-hexafluoropropan-2-yl) phenyl)-2-((4-fluorophenyl)sulfonyl)ethyl)amino)propan-1-ol (200 mg, 0.318 mmol) in dry dichloromethane (10 mL) was cooled to 0° C. under inert atmosphere. To that was added methanesulfonyl chloride (0.030 mL, 0.381 mmol) followed by triethylamine (0.053 mL, 0.381 mmol). The reaction mixture was stirred at 25° C. for 3 h then concentrated under reduced pressure. The residue was treated with hexanes (10 mL) and stirred vigorously for 10 min. The clear hexane layer was decanted out. Similar wash with hexanes was repeated 3 times. The solid residue was dried under vacuum for to yield crude 3-((2-(4-(2-((2,6-difluorobenzyl)oxy)-1,1,1,3,3,3-hexafluoropropan-2-yl)phenyl)-2-((4-fluorophenyl)sulfonyl)ethyl)amino)propyl methanesulfonate as yellow solid (218 mg). The crude material was taken to the next step without further purification. LC/MS (M+1): 708.3.

Step D: 3-(4-(2-((2,6-difluorobenzyl)oxy)-1,1,1,3,3,3-hexafluoropropan-2-yl)phenyl)-3-((4-fluorophenyl)sulfonyl)piperidine

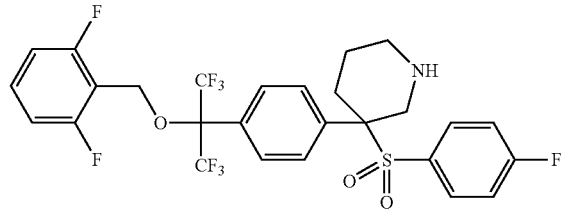 [SMILES: O=S(=O)(c1ccc(F)cc1)C1(c2ccc(C(OCc3c(F)cccc3F)(C(F)(F)F)C(F)(F)F)cc2)CCCNC1]

To a solution of the crude 3-((2-(4-(2-((2,6-difluorobenzyl)oxy)-1,1,1,3,3,3-hexafluoropropan-2-yl)phenyl)-2-((4-fluorophenyl)sulfonyl)ethyl)amino)propyl methanesulfonate (218 mg, from Step C) in dry tetrahydrofuran (10 mL) was added potassium tert-butoxide (34.6 mg, 0.308 mmol) at 0° C. under inert atmosphere. After stirring at room temperature for 3 h, tetrahydrofuran was evaporated under reduced pressure. The residue was diluted with water (25 mL) and extracted with ethyl acetate (3×25 mL). The combined organic phase was washed with water (2×20 mL), brine (40 mL), dried (sodium sulfate), filtered and concentrated under reduced pressure. The crude material was subjected for Prep-HPLC purification (TFA method) to give 3-(4-(2-((2,6-difluorobenzyl)oxy)-1,1,1,3,3,3-hexafluoropropan-2-yl)phenyl)-3-((4-fluorophenyl)sulfonyl)piperidine TFA salt as off-white solid (129.4 mg, 58% yield over two steps). LC/MS (M+1): 612.5; LC retention time: 9.59 min (analytical HPLC Method D); 1H NMR (DMSO-d6, 400 MHz): δ ppm 9.18 (s, 1H), 8.22 (s, 1H), 7.63-7.53 (m, 5H), 7.34-7.19 (m, 6H), 4.66 (dd, J=15.6, 10 Hz, 2H), 4.36 (d, J=13.2 Hz, 1H), 3.75 (d, J=13.2 Hz, 1H), 3.20-3.00 (m, 2H), 2.74 (d, J=13.2 Hz, 1H), 2.53-2.51 (m, 1H), 1.98 (d, J=14.4 Hz, 1H), 1.49 (d, J=13.6 Hz, 1H).

Step E: (3-(4-(2-((2,6-difluorobenzyl)oxy)-1,1,1,3,3,3-hexafluoropropan-2-yl)phenyl)-3-((4-fluorophenyl)sulfonyl)piperidin-1-yl)(4-hydroxy-4-(trifluoromethyl)piperidin-1-yl)methanone

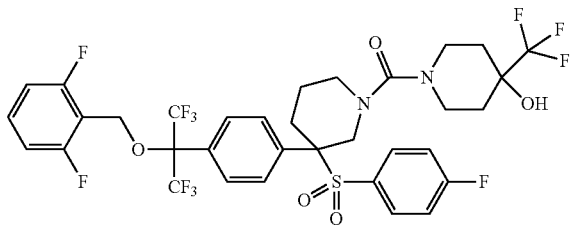 [SMILES: O=C(N1CCC(O)(C(F)(F)F)CC1)N1CCCC(c2ccc(C(OCc3c(F)cccc3F)(C(F)(F)F)C(F)(F)F)cc2)(S(=O)(=O)c2ccc(F)cc2)C1]

Hunig's base (0.015 mL, 0.085 mmol) was added to a suspension of 3-(4-(2-((2,6-difluorobenzyl)oxy)-1,1,1,3,3,3-hexafluoropropan-2-yl)phenyl)-3-((4-fluorophenyl)sulfonyl)piperidine TFA salt (14 mg, 0.017 mmol, 88% pure) and 4-hydroxy-4-(trifluoromethyl)piperidine-1-carbonyl chloride (11.80 mg, 0.051 mmol) in dichloromethane (1 mL). After 1 h at room temperature, the mixture was quenched with ammonium hydroxide (1 drop), stirred for 5 min and concentrated under reduced pressure. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 15 minutes, then a 5-minute hold at 100% B; Flow: 20 mL/min. Fractions containing the desired product were combined and dried via centrifugal evaporation to give Example 2 (11.7 mg, 81% yield). LC/MS (M+1): 807.2; LC retention time: 2.38 min (analytical HPLC Method B); 1H NMR (500 MHz, 1:1 mixture of CDCl$_3$-CD$_3$OD) δ ppm 7.68-7.51 (m, 2H), 7.49-7.23 (m, 5H), 7.03 (dt, J=11.4, 8.3 Hz, 4H), 4.76-4.63 (m, 3H), 3.68-3.42 (m, 3H), 3.22-2.79 (m, 5H), 2.62-2.44 (m, 1H), 1.96-1.76 (m, 2H), 1.68-1.54 (m, 2H), 1.50-1.27 (m, 2H).

Example 3

1-(4-(4-(4-(2-((2,6-difluorobenzyl)oxy)-1,1,1,3,3,3-hexafluoropropan-2-yl)phenyl)-4-((4-fluorophenyl)sulfonyl)piperidine-1-carbonyl)piperazin-1-yl)ethanone

Step A: tert-butyl 4-(4-(2-((2,6-difluorobenzyl)oxy)-1,1,1,3,3,3-hexafluoropropan-2-yl)phenyl)-4-((4-fluorophenyl)sulfonyl)piperidine-1-carboxylate

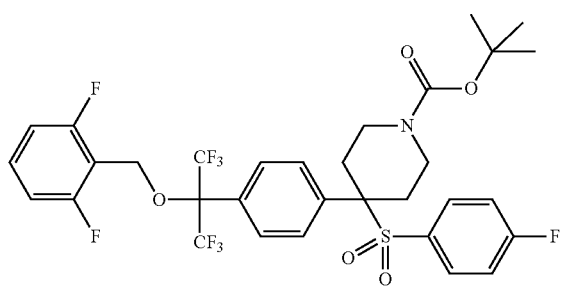 [SMILES: CC(C)(C)OC(=O)N1CCC(c2ccc(C(OCc3c(F)cccc3F)(C(F)(F)F)C(F)(F)F)cc2)(S(=O)(=O)c2ccc(F)cc2)CC1]

A solution of 1,3-difluoro-2-(((1,1,1,3,3,3-hexafluoro-2-(4-(((4-fluorophenyl)sulfonyl)methyl) phenyl)propan-2-yl)oxy)methyl)benzene (2.00 g, 3.69 mmol, from Step C of Example 1) in dry N,N-dimethylformamide (20 mL) was cooled to 0° C. under inert atmosphere. To that was added sodium hydride (0.195 g, 8.11 mmol) followed by tert-butyl bis(2-chloroethyl)carbamate (0.893 g, 3.69 mmol). The reaction mixture was allowed to reach 25° C. and stirred for another 3 h. The starting material remained intact based on TLC analysis. The reaction mixture was heated at 60° C. for 12 h. After cooling to room temperature and quenching with water (20 mL), the mixture was extracted with ethyl acetate (3×25 mL). The combined organic phase was subsequently washed with water (2×50 mL), brine (30 mL), dried (sodium sulfate) and concentrated under reduced pressure to give crude product (2.39 g). LCMS analysis shows 30% formation of tert-butyl 4-(4-(2-((2,6-difluorobenzyl)oxy)-1,1,1,3,3,3-hexafluoropropan-2-yl)phenyl)-4-((4-fluorophenyl)sulfonyl)piperidine-1-carboxylate. The crude material was not purified at this stage and was taken directly for next step. LC/MS (M-55): 656.

Step B: 4-(4-(2-((2,6-difluorobenzyl)oxy)-1,1,1,3,3,3-hexafluoropropan-2-yl)phenyl)-4-((4-fluorophenyl)sulfonyl)piperidine

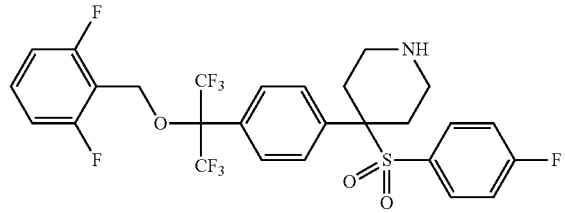 [SMILES: O=S(=O)(c1ccc(F)cc1)C1(c2ccc(C(OCc3c(F)cccc3F)(C(F)(F)F)C(F)(F)F)cc2)CCNCC1]

A solution of crude tert-butyl 4-(4-(2-((2,6-difluorobenzyl)oxy)-1,1,1,3,3,3-hexafluoropropan-2-yl)phenyl)-4-((4-fluorophenyl)sulfonyl)piperidine-1-carboxylate (2.39 g, from Step A) in 4 M dioxane solution of hydrogen chloride (20.20 ml, 81 mmol) was stirred for 3 h at room temperature. After evaporation of solvent under reduced pressure, the residue was dissolved with minimum volume of methanol and triturated with diethyl ether. The resulting off-white precipitate was collected by filtration and further purified by Prep-HPLC (TFA method) to give 4-(4-(2-((2,6-difluorobenzyl)oxy)-1,1,1,3,3,3-hexafluoropropan-2-yl)phenyl)-4-((4-fluorophenyl)sulfonyl)piperidine TFA salt as white solid (440 mg, 17% yield for 2 steps). LC/MS (M+1): 612; LC retention time: 24.77 min (analytical HPLC Method E); 1H NMR (DMSO-d6, 400 MHz): δ ppm 8.58 (br-S, 1H), 8.39 (br-S, 1H), 7.63-7.56 (m, 5H), 7.32 (d, J=7.2 Hz, 3H), 7.23 (t, J=8.0 Hz, 2H), 4.67 (s, 2H), 3.40 (d, J=12 Hz, 2H), 2.82 (d, J=13.6 Hz, 2H), 2.70-2.49 (m, 4H); 19F NMR (376 MHz): δ −69.97, −74.03, −103.5, −114.9.

Step C: 1-(4-(4-(4-(2-((2,6-difluorobenzyl)oxy)-1,1,1,3,3,3-hexafluoropropan-2-yl)phenyl)-4-((4-fluorophenyl)sulfonyl)piperidine-1-carbonyl)piperazin-1-yl)ethanone Example 4

1-(4-(4-(2-((2,6-difluorobenzyl)oxy)-1,1,1,3,3,3-hexafluoropropan-2-yl)phenyl)-4-((4-fluorophenyl)sulfonyl)piperidin-1-yl)-2-(tetrahydro-2H-pyran-4-yl)ethanone

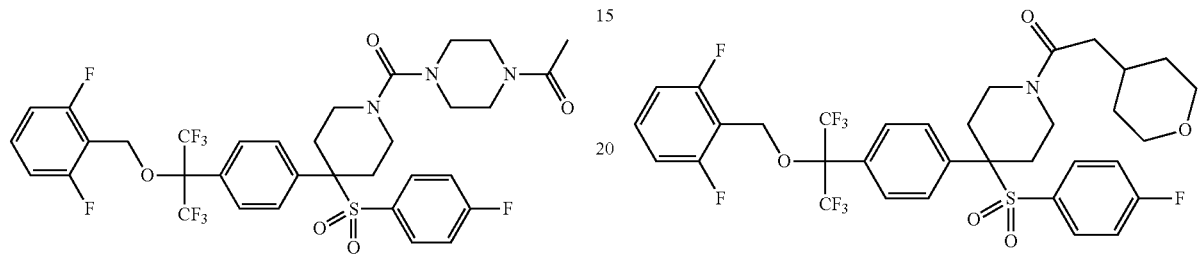

Hunig's base (0.015 mL, 0.087 mmol) was added to a suspension of 4-(4-(2-((2,6-difluorobenzyl)oxy)-1,1,1,3,3,3-hexafluoropropan-2-yl)phenyl)-4-((4-fluorophenyl)sulfonyl)piperidine TFA salt (15 mg, 0.017 mmol, 84% pure) and 4-acetylpiperazine-1-carbonyl chloride (9.93 mg, 0.052 mmol) in dichloromethane (1 mL). After 1 h at room temperature, the mixture was quenched with ammonium hydroxide (1 drop), stirred for 5 min and concentrated under reduced pressure. The crude material was purified via preparative LC/MS with the following conditions: Column: Waters XBridge Shield RP18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation to give Example 3 (10.5 mg, 79% yield). LC/MS (M+1): 766.0; LC retention time: 2.08 min (analytical HPLC Method B); 1H NMR (500 MHz, 1:1 mixture of CDCl$_3$-CD$_3$OD) δ ppm 7.66 (d, J=8.3 Hz, 2H), 7.51-7.37 (m, 4H), 7.09-6.96 (m, 5H), 4.73 (s, 2H), 3.83 (d, J=13.6 Hz, 2H), 3.65-3.58 (m, 2H), 3.57-3.50 (m, 2H), 3.33-3.29 (m, 2H), 3.28-3.22 (m, 2H), 2.92-2.80 (m, 2H), 2.70-2.61 (m, 2H), 2.60-2.51 (m, 2H), 2.13 (s, 3H).

Hunig's base (8.57 μl, 0.049 mmol) was added to a mixture of 4-(4-(2-((2,6-difluorobenzyl)oxy)-1,1,1,3,3,3-hexafluoropropan-2-yl)phenyl)-4-((4-fluorophenyl)sulfonyl)piperidine (10 mg, 0.016 mmol), 2-(tetrahydro-2H-pyran-4-yl)acetic acid (2.83 mg, 0.020 mmol) and (benzotriazol-1-yloxy)tris(dimethylamino)phosphonium hexafluorophosphate (8.68 mg, 0.020 mmol) in acetonitrile (0.5 mL) at room temperature. After 1 h at room temperature, LCMS analysis showed that the reaction was complete. The crude material was purified via preparative LC/MS with the following conditions: Column: Waters XBridge C18, 19×250 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-100% B over 20 minutes, then a 5-minute hold at 100% B; Flow: 20 mL/min. Fractions containing the desired product were combined and dried via centrifugal evaporation to give Example 4 (7.7 mg, 62% yield). LC/MS (M+1): 738.2; LC retention time: 2.30 min (analytical HPLC Method B); 1H NMR (500 MHz, 1:1 mixture of CDCl$_3$-CD$_3$OD) δ ppm 7.64 (d, J=8.3 Hz, 2H), 7.47-7.39 (m, 3H), 7.30-7.22 (m, 2H), 7.06-6.96 (m, 4H), 4.71 (s, 2H), 4.25 (s, 1H), 4.05 (d, J=13.9 Hz, 1H), 3.96-3.85 (m, 2H), 3.46-3.37 (m, 2H), 3.04 (t, J=12.1 Hz, 1H), 2.73 (d, J=12.2 Hz, 1H), 2.67-2.55 (m, 2H), 2.52-2.24 (m, 4H), 2.06-1.93 (m, 1H), 1.72-1.59 (m, 2H), 1.39-1.24 (m, 2H).

The Examples in TABLE 1 below were prepared in the same manner as outlined in the examples above, substituting the appropriate amine intermediate.

TABLE 1

| Example number | Structure | MS observed (M + 1) | HPLC ret. time (min.) | HPLC method |
|---|---|---|---|---|
| 5 | 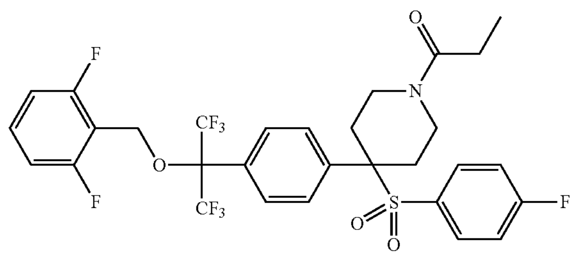 [SMILES: CCC(=O)N1CCC(c2ccc(C(OCc3c(F)cccc3F)(C(F)(F)F)C(F)(F)F)cc2)(S(=O)(=O)c2ccc(F)cc2)CC1] | 668.10 | 2.13 | B |
| 6 | 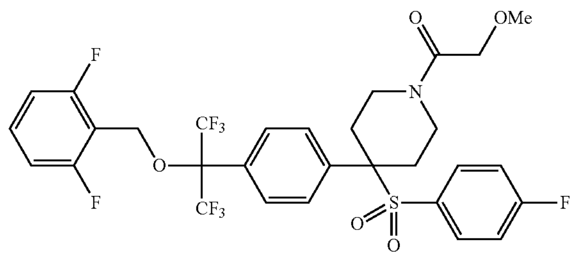 [SMILES: COCC(=O)N1CCC(c2ccc(C(OCc3c(F)cccc3F)(C(F)(F)F)C(F)(F)F)cc2)(S(=O)(=O)c2ccc(F)cc2)CC1] | 684.10 | 2.14 | B |
| 7 | 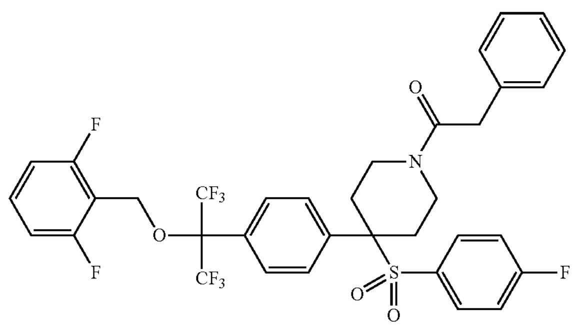 [SMILES: O=C(Cc1ccccc1)N1CCC(c2ccc(C(OCc3c(F)cccc3F)(C(F)(F)F)C(F)(F)F)cc2)(S(=O)(=O)c2ccc(F)cc2)CC1] | 730.20 | 2.37 | A |
| 8 | 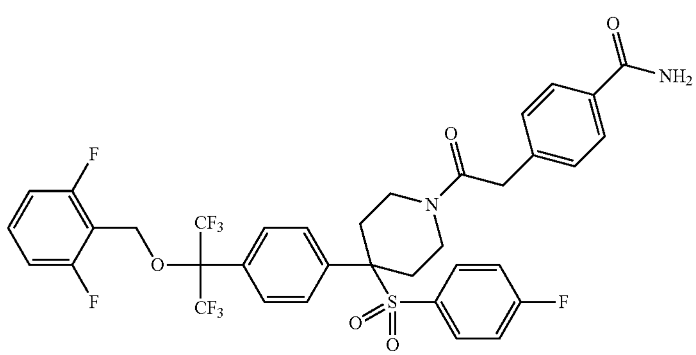 [SMILES: NC(=O)c1ccc(CC(=O)N2CCC(c3ccc(C(OCc4c(F)cccc4F)(C(F)(F)F)C(F)(F)F)cc3)(S(=O)(=O)c3ccc(F)cc3)CC2)cc1] | 773.3 | 2.14 | B |
| 9 | 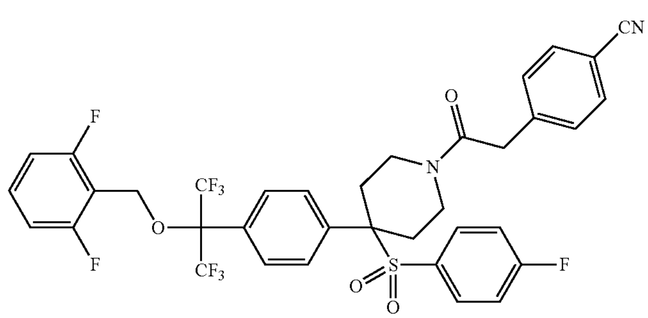 [SMILES: N#Cc1ccc(CC(=O)N2CCC(c3ccc(C(OCc4c(F)cccc4F)(C(F)(F)F)C(F)(F)F)cc3)(S(=O)(=O)c3ccc(F)cc3)CC2)cc1] | 741.2 | 2.28 | B |

TABLE 1-continued
| Example number | Structure | MS observed (M + 1) | HPLC ret. time (min.) | HPLC method |
|---|---|---|---|---|
| 10 | 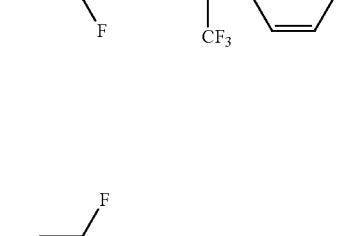 | 731.3 | 2.13 | B |
| 11 | 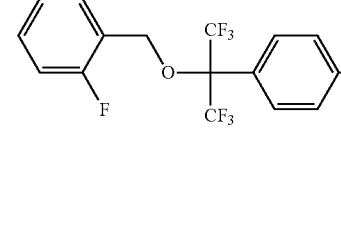 | 731.3 | 2.12 | B |
| 12 | 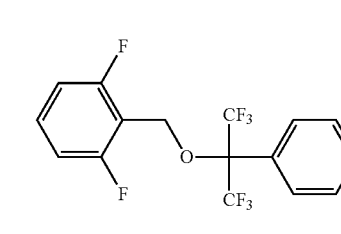 | 717.2 | 2.14 | C |
| 13 | 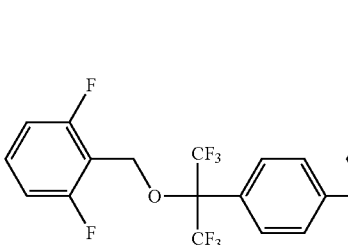 | 766.3 | 1.99 | B |
| 14 | 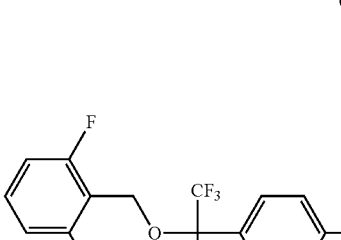 | 765.2 | 2.22 | B |

TABLE 1-continued

| Example number | Structure | MS observed (M + 1) | HPLC ret. time (min.) | HPLC method |
|---|---|---|---|---|
| 15 | 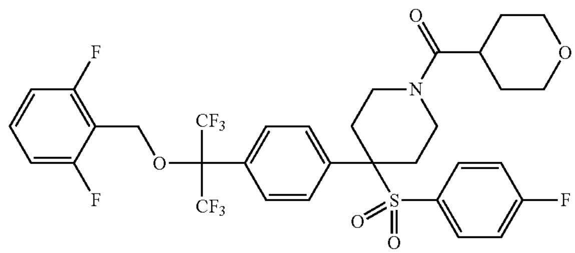 [SMILES: O=C(C1CCOCC1)N1CCC(c2ccc(C(OCc3c(F)cccc3F)(C(F)(F)F)C(F)(F)F)cc2)(S(=O)(=O)c2ccc(F)cc2)CC1] | 724.3 | 2.19 | B |
| 16 | 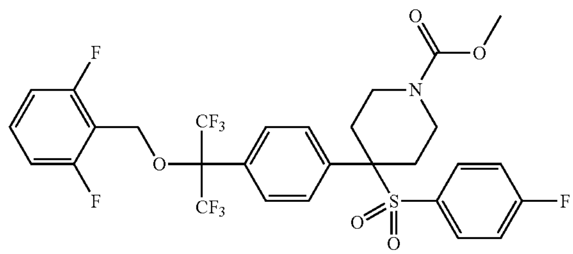 [SMILES: COC(=O)N1CCC(c2ccc(C(OCc3c(F)cccc3F)(C(F)(F)F)C(F)(F)F)cc2)(S(=O)(=O)c2ccc(F)cc2)CC1] | 670.2 | 2.32 | C |
| 17 | 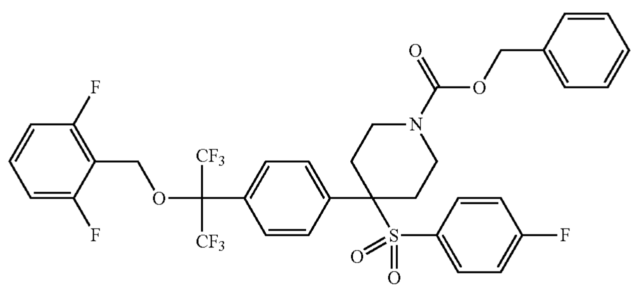 [SMILES: O=C(OCc1ccccc1)N1CCC(c2ccc(C(OCc3c(F)cccc3F)(C(F)(F)F)C(F)(F)F)cc2)(S(=O)(=O)c2ccc(F)cc2)CC1] | 746.1 | 2.55 | B |
| 18 | 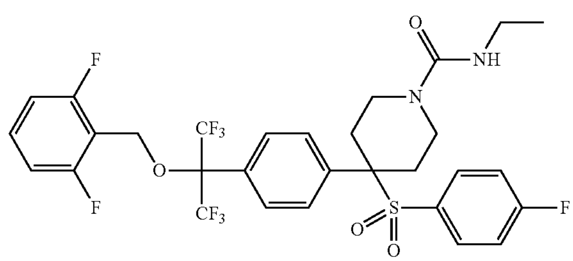 [SMILES: CCNC(=O)N1CCC(c2ccc(C(OCc3c(F)cccc3F)(C(F)(F)F)C(F)(F)F)cc2)(S(=O)(=O)c2ccc(F)cc2)CC1] | 683.2 | 2.15 | B |
| 19 | 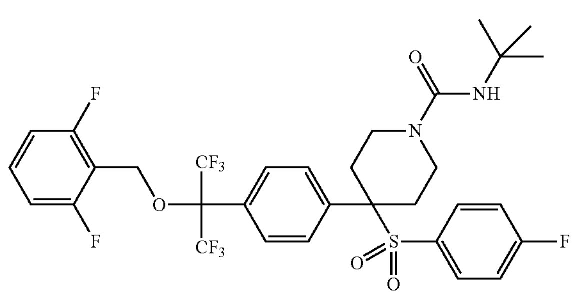 [SMILES: CC(C)(C)NC(=O)N1CCC(c2ccc(C(OCc3c(F)cccc3F)(C(F)(F)F)C(F)(F)F)cc2)(S(=O)(=O)c2ccc(F)cc2)CC1] | 711.2 | 2.35 | B |

TABLE 1-continued

| Example number | Structure | MS observed (M + 1) | HPLC ret. time (min.) | HPLC method |
|---|---|---|---|---|
| 20 | 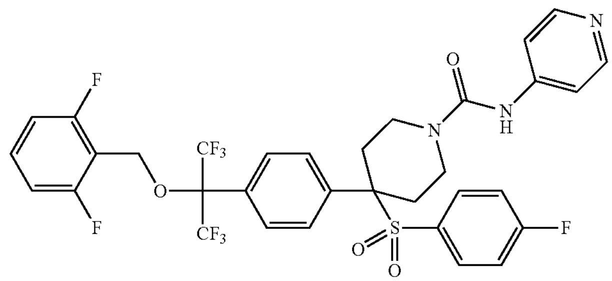 [SMILES: O=C(Nc1ccncc1)N1CCC(c2ccc(C(OCc3c(F)cccc3F)(C(F)(F)F)C(F)(F)F)cc2)(S(=O)(=O)c2ccc(F)cc2)CC1] | 732.2 | 2.14 | B |
| 21 | 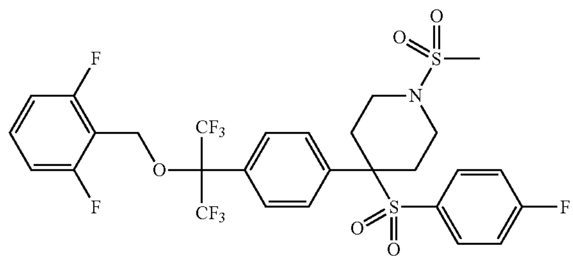 [SMILES: CS(=O)(=O)N1CCC(c2ccc(C(OCc3c(F)cccc3F)(C(F)(F)F)C(F)(F)F)cc2)(S(=O)(=O)c2ccc(F)cc2)CC1] | 690.1 | 2.38 | C |
| 22 | 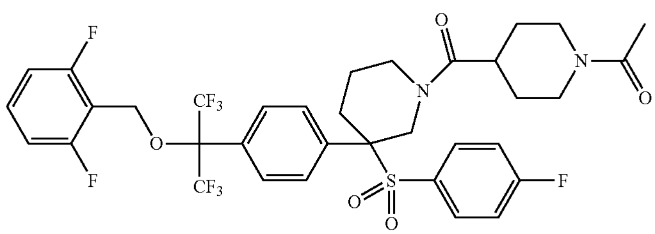 [SMILES: CC(=O)N1CCC(C(=O)N2CCCC(c3ccc(C(OCc4c(F)cccc4F)(C(F)(F)F)C(F)(F)F)cc3)(S(=O)(=O)c3ccc(F)cc3)C2)CC1] | 765.2 | 2.23 | B |

General RORγ SPA Binding Assay

The binding of potential ligands to RORγ is measured by competition with [$^3$H]25-hydroxycholesterol (Perkin Elmer NET674250UC) using a scintillation proximity assay (SPA) binding assay. The ligand binding domain of human RORγ (A262-S507) with an N-terminal His tag is expressed in *E. coli* and purified using nickel affinity chromatography. 15 ug/well RORγ (A262-S507) is incubated with test compound at varying concentrations in 3-fold serial dilution, with final concentrations ranging from 16.6 μM to 0.28 nM for 10 min at room temperature in PBS buffer (Invitrogen #14190-144) containing 0.5% fatty acid free BSA (Gemini Bio-Products, Cat. #700-107P) and 0.1% Glycerol (Sigma Cat# G5516). 10 nM of [$^3$H] 25-hydroxycholesterol is then added, and the reaction is incubated for 10 min. 10 mg/mL of Copper-His Tag-PVT beads (Perkin Elmer cat # RPNQ0095) are added, and the mixture is incubated for 60 min. The reaction is read on a TopCount Microplate scintillation plate reader (Perkin Elmer). The competition data of the test compound over a range of concentrations was plotted as percentage inhibition of radioligand specifically bound in the absence of test compound (percent of total signal). After correcting for non-specific binding, IC$_{50}$ values were determined. The IC$_{50}$ value is defined as the concentration of test compound needed to reduce [$^3$H] 25-hydroxycholesterol specific binding by 50% and is calculated using the four parameter logistic equation to fit the normalized data.

IC$_{50}$ values of the compounds of the invention in the RORγ binding assay are provided below.

| Example # | RORγ Binding IC$_{50}$, uM |
|---|---|
| 1 | 0.170 |
| 2 | 2.630 |
| 3 | 0.219 |
| 4 | 0.057 |
| 5 | 0.093 |
| 6 | 0.062 |
| 7 | 0.166 |
| 8 | 0.167 |
| 9 | 1.387 |
| 10 | 0.148 |
| 11 | 0.195 |
| 12 | 0.191 |
| 13 | 0.340 |
| 14 | 0.314 |
| 15 | 0.056 |
| 16 | 0.140 |
| 17 | 0.488 |
| 18 | 0.063 |
| 19 | 0.128 |
| 20 | 0.093 |
| 21 | 0.118 |

What is claimed is:
1. A compound of the formulae:

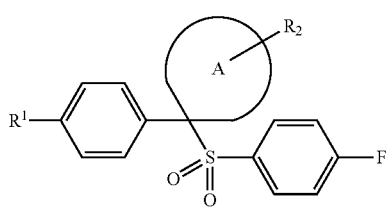

or a stereoisomer or pharmaceutically-acceptable salt thereof;
wherein
A is

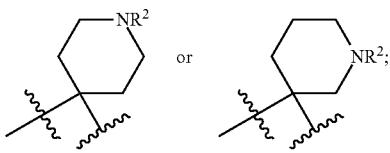

$R^1$ is

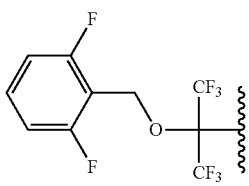

or

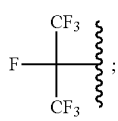

and
$R^2$ is H, S(O)$_2$Me,

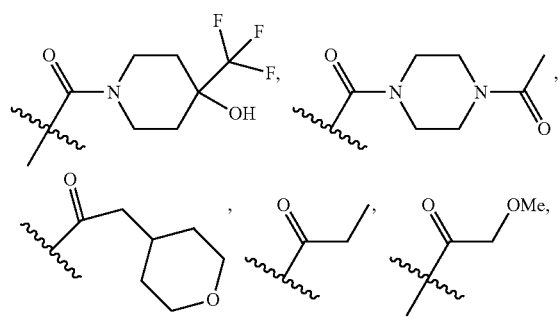

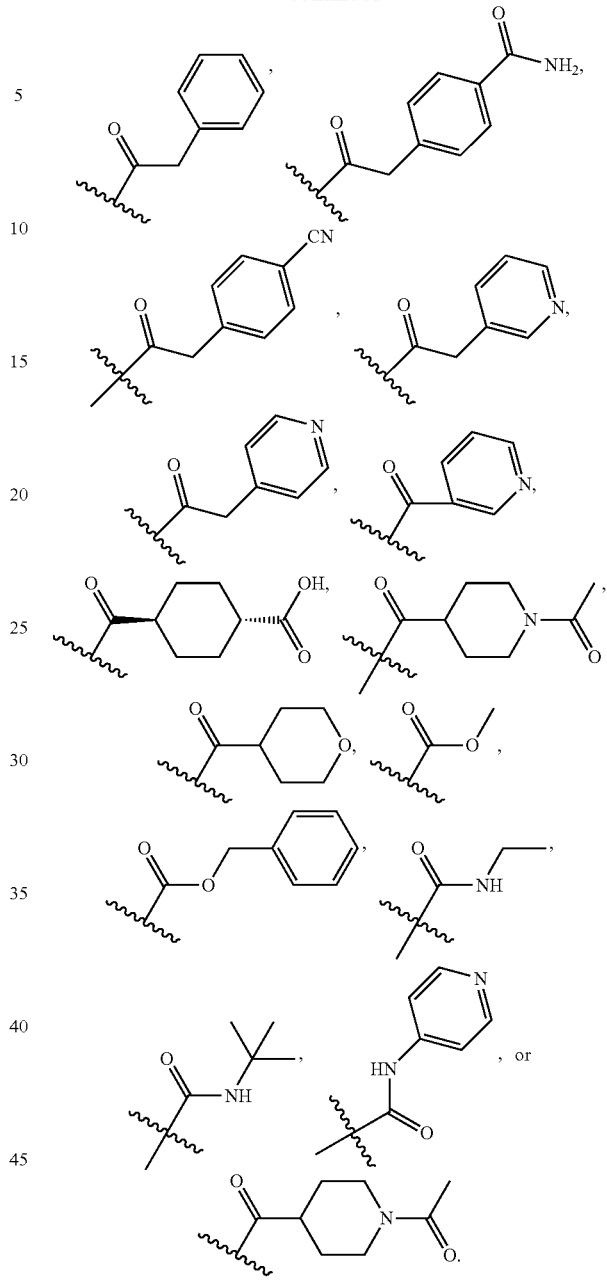

2. A pharmaceutical composition comprising one or more compounds according to claim 1 and a pharmaceutically acceptable carrier or diluent.

3. A method of diagnosing or treating a disease or disorder selected from an autoimmune disease or disorder, asthma, an allergic disease or disorder, a metabolic disease or disorder, and cancer in a subject, said method comprising administering to the subject a therapeutically-effective amount of a compound according to claim 1.

* * * * *